(12) United States Patent
Schlager et al.

(10) Patent No.: US 6,871,147 B2
(45) Date of Patent: Mar. 22, 2005

(54) AUTOMATED METHOD OF IDENTIFYING AND ARCHIVING NUCLEIC ACID SEQUENCES

(75) Inventors: John J. Schlager, Bel Air, MD (US); Richard E. Sweeney, Upper Darby, PA (US); Douglas P. Avery, Crofton, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 58 days.

(21) Appl. No.: 09/961,058

(22) Filed: Sep. 24, 2001

(65) Prior Publication Data

US 2003/0124527 A1 Jul. 3, 2003

Related U.S. Application Data

(60) Provisional application No. 60/235,899, filed on Sep. 28, 2000.

(51) Int. Cl.$^7$ ............................ G01N 33/48; G06F 7/00; C12Q 1/68
(52) U.S. Cl. ............................ 702/19; 702/20; 707/102; 435/6; 536/23.1
(58) Field of Search ..................... 702/19, 20; 707/102; 435/6; 536/23.1

(56) References Cited

PUBLICATIONS

Smith et al. Bio Techniques (1993) vol. 14, No. 6, pp. 1014–1018.*
Burland, T. Methods in Molecular Biology (2000) vol. 132: Bioinformatic methods and protocols, pp. 71–91.*
Shoap E. et al: "Implementation and testing of an automated EST processing and similarity analysis system": System Sciences 1995: Jan. 3, 1995; pp. 52–61; IEEE Comput. Soc.; USA.

Lee A. :"Maximizing online financial data with spreadsheet software ": National Online Meeting Proceedings: May 1987; pp 261–266; Learned Info; USA.

Dimidis S.E. et al: "Design and implementation of a DNA Sequence Processor": System Sciences 1994: Jan. 4, 1994; pp 98–107; IEEE Comput. Soc.; USA.

* cited by examiner

*Primary Examiner*—Mary K. Zeman
(74) *Attorney, Agent, or Firm*—Elizabeth Arwine

(57) ABSTRACT

A method of identifying and archiving a nucleic acid sequence includes a) creating a directory of files in a computer, for storing information related to the nucleic acid sequence; b) inputting a raw nucleic acid sequence into the computer; c) trimming the raw nucleic acid sequence to obtain a trimmed nucleic acid sequence; d) submitting the trimmed nucleic acid sequence electronically to a nucleic acid identification database having a search program and receiving search results electronically from the nucleic acid identification database; e) choosing selective information from each search result and inserting the selective information from each search result into a first electronic spreadsheet; and f) selecting at least one of the search results from the first electronic spreadsheet and inserting the at least one search result into a second electronic spreadsheet.

16 Claims, 3 Drawing Sheets

FIG-3

AUTOMATED METHOD OF IDENTIFYING AND ARCHIVING NUCLEIC ACID SEQUENCES

CROSS-REFERENCE TO RELATED APPLICATIONS

This application claims the benefit of priority from U.S. provisional patent application Ser. No. 60/235,899 filed Sep. 28, 2000, which is hereby incorporated by reference.

STATEMENT OF GOVERNMENT INTEREST

The invention described herein may be manufactured and used by or for the Government of the United States of America for government purposes without the payment of any royalties therefor.

REFERENCE TO COMPUTER PROGRAM LISTING APPENDIX

A Computer Program Listing Appendix is hereby expressly incorporated by reference. The Computer Program Listing Appendix includes two duplicate compact discs. The files on each compact disc, the date created and the file size in bytes are:

| File Name | Date Created | Size (bytes) |
| --- | --- | --- |
| MakeHelp.bat | Sep. 27, 2000 | 1,594 |
| newlibrarynamedlg.cpp | Oct. 05, 2000 | 1,926 |
| newlibrarynamedlg.h | Sep. 29, 2000 | 883 |
| resource.h | Feb. 06, 2001 | 8,530 |
| resource.hm | Feb. 06, 2001 | 4,528 |
| startdlg.cpp | Oct. 23, 2000 | 3,742 |
| startdlg.h | Oct. 23, 2000 | 1,093 |
| StdAfx.cpp | Oct. 11, 2000 | 221 |
| StdAfx.h | Oct. 03, 2000 | 602 |
| SubtractionLibraryUtility.cpp | Oct. 11, 2000 | 4,047 |
| SubtractionLibraryUtility.h | Feb. 06, 2001 | 6,385 |
| SubtractionLibraryUtility.hpj | Feb. 06, 2001 | 2,624 |
| SubtractionLibraryUtility.rc | Jul. 25, 2001 | 28,316 |
| SubtractionLibraryUtilityDlg.cpp | Jun. 21, 2001 | 209,771 |
| SubtractionLibraryUtilityDlg.h | Apr. 16, 2001 | 6,943 |
| SubtractionLibraryUtility.hm | Aug. 9, 2001 | 663 |
| TimedMessage.cpp | Oct. 27, 2000 | 1,718 |
| TimedMessage.h | Oct. 27, 2000 | 875 |
| trimdialog.cpp | Nov. 06, 2000 | 119,594 |
| trimdialog.h | Nov. 06, 2000 | 4,099 |
| TUTORIAL PRIMERS.VEC | Jun. 08, 2001 | 2,039 |
| TUTORIAL001.Seq | Jun. 11, 2001 | 640 |

BACKGROUND OF THE INVENTION

The present invention relates in general to identifying nucleic acid sequences and in particular to an automated method for identifying nucleic acid sequences and electronically storing information related to the nucleic acid sequences.

The present invention is useful, for example, for researchers using the subtraction library technique to determine regulation of mRNA, researchers using a high throughput technique for identification of DNA or cDNA nucleotide sequences and researchers with data containing many unknown DNA sequences that require revisiting a nucleic acid identification database on a regular basis.

In the United States, the National Institutes of Health's (NIH) National Center for Biotechnological Information (NCBI) maintains databases with information about each nucleotide sequence that has been submitted to it. The NCBI database is accessible to the general public. There is one record for each sequence in the non-repeating database (NR) or multiple matching records in the expression sequence tags (EST) database. The NCBI database is updated daily and has become one of the world's largest repositories of protein and genetic data. Other publicly available databases are located in Europe and Japan. In addition, some private entities maintain nucleic acid identification databases that are not generally available to the public.

An example of the use of a nucleic acid identification database involves the subtraction library technique. Using a subtraction library technique, one can produce hundreds of cDNA protein fragments that are either up regulated or down regulated in response to a stimulus defined by different experimental conditions. The sequence of base pairs for each fragment can be determined using DNA sequencers, producing files of "raw" sequences, generally in an electronic format. To make use of these data, each raw sequence needs to be identified as a subset of a known protein, mRNA, gene, or DNA sequence for use in further analysis. The identification can be done by requesting that NCBI match the sequence against all of the known sequences in its database and return information about the most similar matching items. There will usually be many possible matches with reams of data returned for each match. The amount of data generated becomes unmanageable very quickly. The present invention helps a researcher organize and use data obtained from a nucleic acid identification database.

In the past, when using a publicly available database such as the NCBI database, the identification of each nucleic acid sequence involved: 1) visually scanning the nucleic acid sequence; 2) deleting the vector and adaptor sequences; 3) electronically pasting the edited sequence into a web-based search request form for submission to the Basic Local Alignment Search Tool (BLAST) page on the NCBI website; 4) waiting on-line for data analysis and transfer; 5) printing the search results for later review; and 6) selecting certain of the sequence identifier search results and typing them into a spreadsheet for specific data capture, archiving and subsequent sequence analysis. During review of the hard (paper) copy sequence alignments, it was common to revisit the BLAST site on the web to obtain further information. This further information was available through hyperlinks embedded in the original output, but was not accessible when reviewing a paper copy.

The present invention automates all of the steps that were previously done by hand, starting from the raw sequence files (produced by the nucleic acid sequencers) through to the creation of a complete library file that contains identification of the nucleic acid sequences in an individual nucleic acid library sample set. It is estimated that the invention reduces the data capture and review time required for nucleic acid sequence identification by as much as 90 percent.

SUMMARY OF THE INVENTION

It is an object of the invention to provide a method of identifying nucleic acid sequences that automates repetitive tasks that had been performed manually. One repetitive task is submitting a nucleic acid sequence to a nucleic acid identification database. In one embodiment of the invention, this task is the submission of a web-based search request for a nucleic acid sequence to the BLAST server at NCBI and the eventual return of the hypertext (html) formatted search results. In the past, the search results were printed for storage and later review. In addition to consuming paper, hardcopy storage of these results ignored important hyperlink information embedded in the returned files. The present invention accesses a nucleic acid identification database (such as NCBI's server) electronically and stores all returned data electronically rather than as hardcopy.

A second repetitive task involves the transfer of information from web-page printouts into spreadsheets. In addition to inviting typographical errors, the manual process was extremely time-consuming. The present invention maintains all information electronically so that this transfer of information from the hypertext search results to spreadsheets is performed under computer program control.

Another object of the invention is to use artificial intelligence to select positions for nucleic acid trimming. The raw nucleic acid sequence exists as a set of letters (A, G, C, T, or N) that indicate the nucleic acid code identified in the sequenced material. The sequencer uses the letter "N" to indicate a nucleotide that could not be identified. The sequenced material may contain portions of the cloning vector and the primer adapter used for sequence manipulation, such as selective isolation and amplification. Therefore, each end of the raw sequence may have strings of letters that do not belong to the DNA sequence (EST or mRNA) that was isolated. The DNA trimming operation requires selection and removal of this extraneous, experimentally added information. A user can become fairly adept at locating the trim boundaries, but the time involved in running an editor program, loading the sequence and saving the trimmed results outweighs the amount of time devoted to locating trim positions. In the present invention, the loading, trimming and saving of the raw sequences is done under computer program control. Because a user cannot recognize the correct endpoints faster than a computer can find them in the 300–1500 nucleotides of a raw sequence, a template matching algorithm is used to provide an initial guess for the proper trim positions. This guess is presented graphically to the user, who may accept or modify it.

Still another object of the invention is to impose a file storage scheme to organize the multitude of generated electronic files. The invention generates a multitude of electronic files of different types that are associated with different libraries. A directory structure is used that allows the files to be organized by information type and by DNA library. Because it is convenient to maintain any previous scheme for naming the stored DNA isolates, the invention uses a file naming scheme that appends appropriate designators to the names originally assigned to the isolates.

Yet another object of the invention is to use embedded hyperlinks for quick access to related files. For example, a search on the NCBI databases for a single EST from the mRNA isolate normally returns a set of possible matches. This set requires review to determine which match (if any) best identifies the protein associated with the translated EST. This review demands expert knowledge and judgment. However, to accelerate this process, the invention captures those hyperlinks into the NCBI database that are returned with each protein match, creates new hyperlinks to any intermediate files that are created and incorporates these hyperlinks into the final DNA library. This data file and web page hyperlinking allows the expert reviewer single click access to any of the underlying component files, and the ability to link to specific information on the NCBI site for further analysis or access to web-based research articles related to the identified target sequence. Once linked into the NCBI site, associated hyperlinks can be used to perform in-depth data and information gathering (PubMed, other genome databases, etc.) for an individual sequence.

In accordance with the present invention, a method of identifying and archiving a nucleic acid sequence comprises a) creating a directory of files in a computer, for storing information related to the nucleic acid sequence; b) inputting a raw nucleic acid sequence into the computer; c) trimming the raw nucleic acid sequence to obtain a trimmed nucleic acid sequence; d) submitting the trimmed nucleic acid sequence electronically to a nucleic acid identification database having a search program and receiving search results electronically from the nucleic acid identification database; e) choosing selective information from each search result and inserting the selective information from each search result into a first electronic spreadsheet; f) selecting at least one of the search results from the first electronic spreadsheet and inserting the at least one search result into a second electronic spreadsheet.

Another aspect of the invention is a computer readable medium, such as a compact disc, containing a computer program for performing the above-described method.

Further objects, features and advantages of the invention will become apparent from the following detailed description taken in conjunction with the following drawing.

BRIEF DESCRIPTION OF THE DRAWING

FIG. 3 (SEQ ID NOS 7, 9 and 12–16) shows a Trimming Interface computer display.

DETAILED DESCRIPTION OF THE PREFERRED EMBODIMENTS

Definitions

Figure 1:
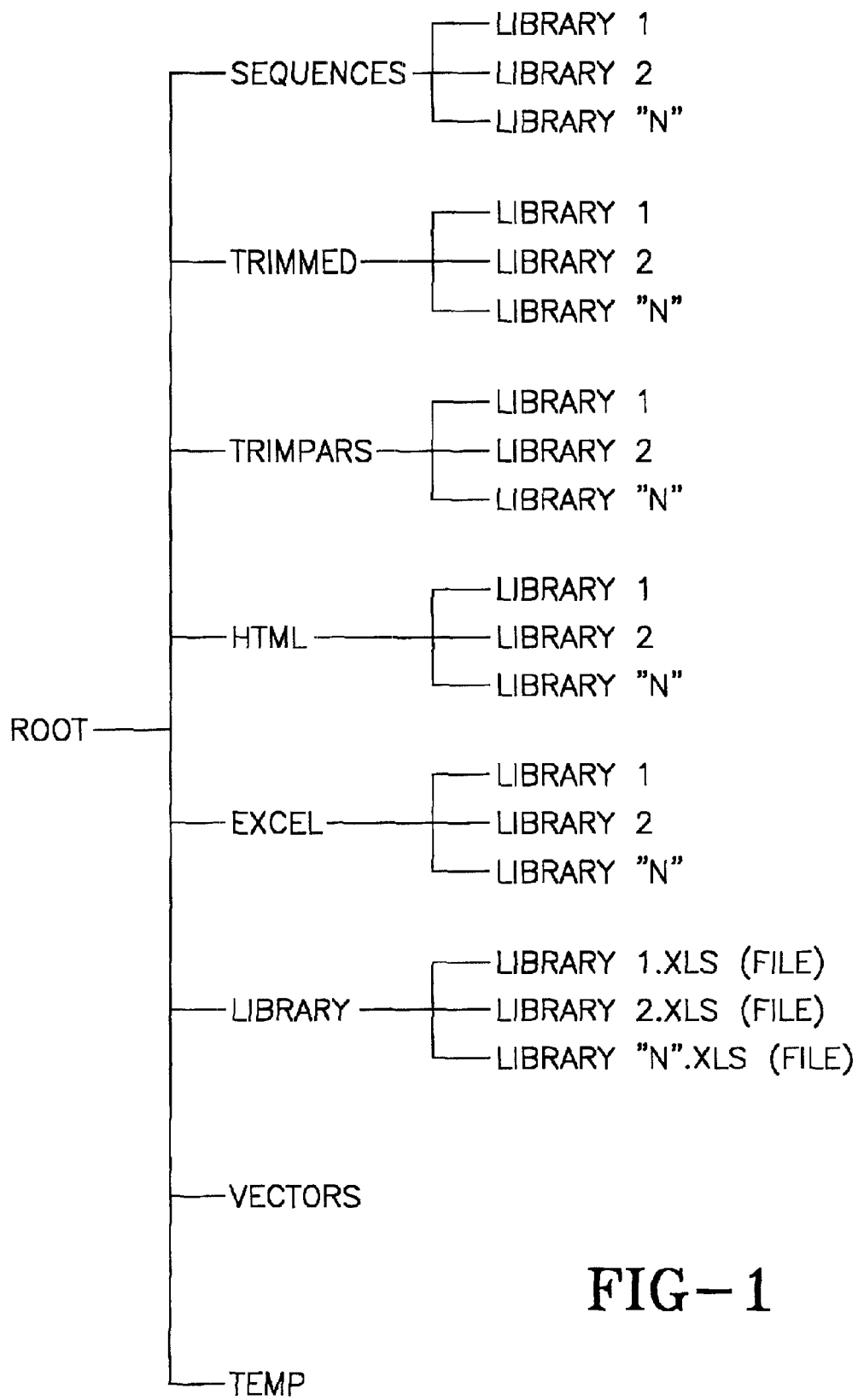
FIG. 1 shows a file directory structure for one embodiment of the invention.

Sequence files: Files that contain a text string such as "AGGTCGT" where the letters are used to indicate the sequence of bases in polynucleic acid. Raw sequence files contain sequence portions from cloning vector, attachment adapters, and cDNA (mRNA) fragments.

Subtraction libraries: Subtraction libraries are selected cDNA formed from mRNA molecules that have been isolated to enhance their different mRNA abundance in two mRNA pools that are being compared. If the two pools are from cells of the same type where one group has been exposed to some stimulus, then the difference in cDNA (from mRNA) should be due to a cellular response to the stimulus. Depending on the starting point used, the subtraction library will consist of mRNA that is either up-regulated or down-regulated in response to the stimulus.

Trim parameters file: These files store the positions used to trim adapters and vector from the cDNA fragment of interest. This allows the user to review and alter the selected trimming positions.

HTML files: These files are returned (over the internet) from the BLAST search engines at NCBI. These files are normally viewed with a web browser.

BLAST: A computer program suite, the Basic Local Alignment Search Tool (BLAST), that runs at NCBI and which matches a nucleotide sequence (represented by a string of letters coded for the nucleic acid bases A, G, T, and C) against the sequences stored in the database records. Information about the records that match the search sequence and about the degree of the matches is returned from the search tool.

Vector files: These files contain information about attachment adapters and cloning vectors. These can be used to configure the trimming operation.

Trimmed sequence files: These files contain a text string such as "AGGTCGT" where the letters are used to indicate the sequence of bases in a nucleic acid polynucleotide. Trimmed sequence files contain only sequence portions isolated while building the subtraction library.

The method of the invention is implemented by a computer program that is loaded into a general purpose computer. The computer is electronically connected to a nucleic acid identification database having a search program, such as the NCBI database. The computer also contains a commercially available spreadsheet program, such as Microsoft Excel®, and a browser program, such as Microsoft Internet Explorer®. In the embodiment of the invention described below, the nucleic acid identification database is the NCBI database and the spreadsheet program is Microsoft Excel®. However, it should be understood that other nucleic acid identification databases may be used and, similarly, other spreadsheet and browser programs may be used. Furthermore, the described embodiment relates to the subtraction library technique, but is equally applicable to the creation, storage and management of any type of DNA sequence data or DNA library.

Computer Program Overview

The program operates in one of five program modes or steps. All modes except the first mode operate on a set of files selected by the user. The first mode allows selection of an existing DNA library or automatic creation of the directory structures for a new DNA library. The data inputs into this program are the raw sequence files created by a DNA sequencer for each fragment from the DNA library. The raw sequence files are moved manually into a library's raw sequence directory before processing can begin.

A raw sequence file may contain extraneous sequence from an expression vector or DNA adaptors used in the amplification process. The second program mode allows the user to remove the extraneous portions from the unidentified sequence. The third program mode uses the Internet to submit each unknown sequence to the BLAST program on the NCBI server and captures the search results in HTML format. The fourth program mode allows the user to organize the information from each HTML search result file into a Microsoft Excel® file containing the ranked identification results for unknown sequence. Based on the protein identity and match scoring information presented in this file, the user may indicate which sequence matches to preserve by marking a field in this intermediate Excel® file. By default, a fixed number (20) of the highest scoring sequence matches are preserved, but this number can be modified by the user.

The last program mode allows the best or selected matches to each unknown sequence to be compiled into the final DNA library file. It is this final, Microsoft Excel® formatted file that provides the starting point for the user to analyze the DNA library. Hyperlinks in this file allow the researcher to navigate to any of the intermediate files or into the NCBI database for further information on all DNA sequences of interest in the library file. The DNA library file created by this program provides the reviewer a direct gateway into an interconnected DNA library data set, providing a valuable tool for analysis or new hypothesis generation.

Data Management

In the laboratory, plasmids isolated from bacterial colonies generated from a cloned DNA library are usually given some name based upon an experimentally determined/structured naming system. This name is typically used in laboratory notebooks and on labels for preservation vials. It is important that any naming scheme used by a data management program must not place restrictions on the laboratory's naming convention. The name assigned to an isolate under the laboratory's naming convention is called the "base name" which becomes part of the name of all files created on a specific sequence. These intermediate files created by the software will be named using the base name with an appended suffix and file extension. Some characters are removed from the base names of intermediate files because they interfere with the linking strings.

The processing of each raw data file results in the creation of four intermediate files: three text files (trimmed sequence file: name_nv.seq; vector pairs sequence file; and the BLAST results file: name.html) and one Excel® file (name_searched-database-name.xls). Information from the Excel® files containing the parsed HTML information on each isolated cDNA fragment is combined into a single (Excel® formatted) Subtraction Library File. With the multitude of related files created by this program for each subtraction library, extensive hyper-linking between the files allows the researcher to quickly review related information used to build the subtraction library including all intermediate files and the information link to the sequence and the known data at the NCBI databases. The software automatically creates the required directories and files when the program is first run. Subdirectories are also created when the user runs the program and creates a given library name. These subdirectories under the user defined library name are for automatic storage of sequence files and associated data on individual sequences from that library. The files created by the software should remain in fixed locations after the links have been created to insure maintenance of file links. Therefore, files must not be moved from the creation subdirectory or these links will be lost. However, the user can recreate the links by moving the existing or creating new sequence html files into a preferred name directory.

A directory structure is used to organize the multitude of files. The main or root directory is the directory in which the program has been installed. It is convenient (though not required) that this root directory be created on a shared network drive, so that multiple users within a group can access the data. In one embodiment of the invention, the only restriction is that the root directory not be "C:\BLAST". The "C:\BLAST" directory will be created (on a user's local drive) the first time a user runs the program and is used to manage scheduled NCBI database searches as well as to store a particular user's preferences. Again, all directories under the root are also created the first time the program is run and the program automatically creates subdirectories when the user creates a named individual subtraction library during the first step of the program.

A file naming convention is used that creates all data files associated with a particular isolate with names based upon the user-defined identifier given to the raw sequence file. Suffixes are appended to the base names to name files related to the original sequence file. There are 7 different types of files used by the program. Four types (vector files; raw sequence files; trimmed sequence files; and trimming parameter files) are formatted as ASCII text files. The fifth type is an HTML formatted file captured over the Internet from the database server at NCBI. The sixth and seventh types are formatted as Microsoft Excel® files.

TABLE 1

Suffixes Applied to Base Names for cDNA Plasmid Isolates

| Suffix | Extension | Type | Contains |
|---|---|---|---|
| none | .seq | raw sequence file | the raw nucleotide sequence |
| none | .xls | Microsoft Excel ® file | formatted "best" identifications (one row per mRNA isolate) |
| _NV | .seq | trimmed sequence file | the cDNA nucleotide sequence trimmed of adaptors and vector |
| _TRIMPARS | .txt | text file | trimming parameters |
| _EST* | .html | HTML file | search results from EST database |
| _EST | .xls | Microsoft Excel ® file | formatted EST results and graph |
| _NR | .html | HTML file | search results from NR database |
| _NR | .xls | Microsoft Excel ® file | formatted NR results and graph |

*Note:
there are similar files and extensions for ten other NCBI databases

The files used are organized into the directory structure shown in FIG. 1. There are two levels of directories defined. The main level directories are the first level directories under the root directory and are used to separate the different types of files used or created by the program. All directories (or folders) are created automatically the first time the program is run. The main level directories are:

| | |
|---|---|
| SEQUENCES | for raw sequence files |
| TRIMMED | for trimmed sequence files |
| TRIMPARS | for trimming parameter files |
| HTML | for HTML files |
| EXCEL | for blast result excel files |
| LIBRARY | for library excel files |
| VECTORS | for vector definition files |
| TEMP | for internal storage of temporary files |

There is a second level subdirectory created for each subtraction library under the SEQUENCE, TRIMMED, TRIMPARS, HTML, and EXCEL directories. Each subdirectory is named with the term or code for the subtraction library. This name is assigned when the user chooses to create a new subtraction library. For each subtraction library created, there will be a subtraction library Excel file created in the LIBRARY main directory. The data for a subtraction library can be thought of as "flowing" between the subtraction library's directories under each of the SEQUENCE, TRIMMED, HTML, and EXCEL directories, and finally to the subtraction library's file under the LIBRARY directory.

The sequence files, which are output by the DNA sequencer, should be copied manually into the desired subtraction library's subdirectory under the SEQUENCES main directory. Although the program can pull the raw sequence files from any location, it makes sense to store them in an area related to the library of which they are a part. The Excel formatted subtraction library file is designed to allow a side-by-side comparison of the proteins targeted by each of the cDNA (mRNA) fragments in the subtraction library. This file, which is the entry point for analyzing the data, provides summary information about each cDNA's identity and links into related intermediate files and into the NCBI databases. These links allow the researcher to explore perceived relationships about a cell's functional response to the controlled stimulus or the set of experimental conditions associated with the subtraction library.

Trimming the Raw Sequence Files

If DNA adapters, such as used for polymerase chain reaction (PCR) amplification, and/or a cloning technique are used as is done when constructing a subtraction library prior to sequence analysis, the fragments will have known experimentally added DNA sequence at either end of the cDNA fragment sequence. Due to this cloning scheme, the resulting sequence contains the sequence arrangement vector/adapter-cDNA fragment-adapter/vector. After PCR amplification and DNA cloning, single bacterial colony isolation and plasmid DNA purification, the known site for cDNA begins just beyond one end of the inserted 5' vector-adapter sequence and ends just prior to the inserted 3' adapter-vector.

Sequencing from one side of the insert is assigned as a "forward" sequencing direction that can be arbitrarily given by the researcher such as based on the M13 priming site or on the vector's origin of replication (ORF). Sequencing starting from the other side is assigned the reverse sequencing direction. The nucleotide sequence determined by the DNA sequencer is stored in a text file as an ordered set of letters (A, C, G, T, N) representing the nucleotides. In one embodiment of the invention, the trimming step finds the 5' and 3' end sequences and a confirmatory sequence 20 nucleotides into the cloning vector and removes these sequences from the cDNA. The confirmatory sequence is chosen by the user, can be from any region of known vector sequence, and placed with the 5' and 3' adapter sequences in a specific file within the Vectors subdirectory. The output of the trimming step gives match percent, size of the fragment, as well as many other parameters (discussed in more detail below), under user control to assign the trim site for removal of these experimentally added sequences. The resultant trimmed sequence is stored in a file (name_nv.seq; where nv refers to "no vector") and the original raw sequence is retained in a raw sequence file.

The sequences in the raw sequence files start with known sequence, generally a small portion of the cloning vector, followed, in order, by a 5' end adapter, the cDNA fragment-of-interest, the 3' end adapter, and more of the cloning vector. The trimming step removes the known portions of the vector and adapter sections of DNA from the sequence to leave only the DNA fragment-of-interest. It is this DNA portion that represents a fragment of one of the mRNA molecules in the library. The known sequences for the adapters and vectors used when the subtraction library was built are read from a user created vectors file. Since the cDNA sequence fragment exists between the 5' and 3' ending adapters, by identifying the locations of the end adapter sequences in the raw sequence, the fragment-of-interest (the nucleotides between the adapters) can be determined.

A complicating factor is that the adapter/fragment-of-interest/adapter portion can insert into the circular cloning vector in one of two orientations (especially in blunt-end cloning) which is arbitrarily referred to as "plus" and "minus" sequence direction. When one searches for the adapters, one must consider both cases. To add an additional degree of confidence in the adapter search, the trimming operation also looks for a known segment of the cloning vector that would occur past the insert-3' adaptor sequence. In general, the reliability of the DNA sequencer output due to conditions and robustness of the sequencing reaction typically starts fairly high in base calling accuracy but begins to fail generally after several hundred nucleotides. Since sequencing starts near one side of the insert, the first adapter (the starting or 5' adapter) should always be found. If the second adapter (the ending or 3' adapter) and a confirmation sequence can also be found, the researcher can have a high degree of confidence that the fragment-of-interest is correctly represented by the portion of the raw sequence between the adapters. If the 3' adapter can't be found, then it is possible that the quality of the DNA sequencing reaction and therefore the sequencer's DNA output may have degraded before complete coverage of the entire insert sequence, which is generally due to a long cDNA insert. It would be proper to keep all nucleotides after the first adapter as the fragment-of-interest for further analysis and not trim the 3' end.

The computer program looks for a known portion of the cloning vector downstream from the second adapter sequence as a confirmation that the DNA sequencer output was of high quality while the insert was being sequenced. The confirmation sequence to be found depends upon the direction (forward or reverse, which is assigned by the user) chosen for the sequencing. There is no need to assign the sequencing direction for the program, since it searches for both a forward and a reverse confirmation sequence in this step to find the best adaptor/primer match.

The search for the sequence match is done automatically for the user. The program's decision about the location of the fragment-of-interest is presented in highlighted regions via a visual display (such as a computer monitor) to the user. The locations of the starting and ending adapters can be altered, if desired, by clicking and dragging a slide bar below the sequence display window to move the highlighted section to another area of interest. It is these highlighted locations that control the portions of the raw sequence that are removed in the trimming operation where the sequence is retained at the 3' base of the 5' primer and the 5' base of the 3' primer and automatically placed into a trimmed sequence file (name_nv.seq; where_nv refers to no vector sequence).

The locations where the raw sequence is trimmed are stored for the user for later referral by the program in a trimming parameters file. This file enables the program to reconstruct the trimming applied by the user when the user reviews a previous trimming operation. Each trimming parameter file has only a single line of information. The file is formatted as a text file. The first and only line of the file has seven integer values numbers on it, separated by spaces.

The seven values are:

1st 5' adapter score, positive insert orientation
2nd 3' adapter score, positive insert orientation
3rd 5' adapter score, negative insert orientation
4th 3' adapter score, negative insert orientation
5th nucleotide number (starting with 1) of the first nucleotide in the raw sequence to be saved
6th nucleotide number (starting with 1) of the last nucleotide in the raw sequence to be saved
7th a flag indicating the insertion orientation that was assumed (0 = negative, 1 = positive)

Identifying the Sequence Molecule from the DNA Fragment

In one embodiment of the invention, sequence identification occurs by automated searching of the database(s) maintained by the NCBI. There are many cDNA fragments produced in a single subtraction library, and these cDNAs are formed from parts of mRNA molecules whose abundance was changed from another comparable population of mRNA molecules. Ideally, many thousands of bacterial colonies could be randomly selected (without duplication) and processed to guarantee that all fragments from all mRNA molecules in the library are examined in proportion to the abundance of the mRNA molecules. More practically, a large number of randomly selected colonies are processed depending upon the library's diversity. The nucleotide sequence of each cDNA fragment is searched against the databases at NCBI, where daily updated information is stored on all known (public) protein and DNA sequences. Once the identities are associated with mRNA for target proteins, or with gene or EST DNA, the researcher will have initial data to support hypotheses that the experimentally derived state shown in the cell's response to the stimulus has increased (or decreased) the production of a specific set of proteins and therefore enhanced (or diminished) specific pathways or cellular function.

Each trimmed sequence file contains a string of letters representing the nucleotides in a cDNA fragment built from mRNA to generate the subtraction library. In this step of the invention, the user may specify which of the NCBI databases that will be searched and can limit the number of brief descriptions and detailed alignments that are reported by NCBI for each database searched. The program formats the trimmed sequences and search specifications into a search request recognized by the NCBI website and establishes a connection to the server. The search program on the NCBI server is run to find database records with nucleotide sequences that best match the trimmed sequence. The NCBI program sends information about the matching records back to the subtraction library program, where the data is automatically stored in an HTML file in the proper directory. Because the server at NCBI can, at times of heavy usage, respond very slowly, the computer program includes wait features as well as a feature that allows the user to schedule the search request to be sent to the NCBI website at some future, off-peak time. Searching a selected set of trimmed sequence files against the NCBI databases creates a set of HTML formatted results files. If desired, these files can be viewed with a web browser.

Table 2. below is an example of an HTML file returned from the NCBI "blast" search program following a sequence search of the NCBI non-repeating (NR) library of sequences. Hyperlink text are shown in Table 2. in bold font. For the purpose of the description of Table 2. given below, dashed lines have been inserted to delineate the sections of the HTML file. The only time that a user would see an HTML file would be if they clicked on the hyperlink provided in the fourth columns of either the intermediate Excel files or the final library Excel file.

The first section of the HTML file includes three lines that show a program identification tag, the complete filename of the "trimmed" sequence file containing the searched sequence, and the date that the search was performed. The second section contains information describing the NCBI search results type, a paragraph describing the search filters used, a reference associated with the best match NCBI record, and the number of database sequence records (and nucleotides) searched. The third section contains an ordered listing of the matches found during the NCBI search. Only the first two sequence matches of a user-defined match limit (program default is 20 matches) are shown, for example. The "score" (a calculated value of the number of nucleotides matching between the search sequence and the sequence stored in the NCBI database record, incorporating penalties for gaps and mismatches) and the "E" value (the probability that a random sequence of nucleotides of the same length as the search sequence would match the sequence stored in the NCBI record) are used to determined the order, with the best matches presented at the top of the list. The hyperlink at the left of each list entry link the user directly to the NCBI database record that produced the match represented by the entry. The hyperlink at the right (the probability number E) links the user to the start of a detailed presentation for the match represented by the list entry. The fourth section contains sets of detailed information about each match. The details for both matches are shown in Table 2. The detailed information for each match includes the number of matching nucleotides and gaps, the direction (sense/anti-sense) of the sequence pairings, and a top-over-bottom sequence similarity presentation of the matching sequences showing where individual nucleotides match. The last section presents information related to the operating conditions of the NCBI search program.

TABLE 2

```
Schlager's BLAST UTILITY, RESECO @1999
Results from file \\r5840\pub\MolTox\blast\TRIMMED\MB2D\M2r02_NV.SEQ
BLAST search done 4/5/2000
HTTP/1.0 200 OK MIME-Version: 1.0 Content-type: text/html
    The query sequence for this search has been filtered. Filtering
eliminates low complexity regions that commonly give spuriously high
scores that reflect compositional bias rather than significant position-by-
position alignment. Filtering can eliminate these potentially confounding
matches (e.g., hits against proline-rich regions or poly-A tails) from the
blast reports, leaving regions whose blast statistics reflect the specificity
of their pairwise alignment.
BLASTN 2.0.11 [Jan-20-2000]
Reference: Altschul, Stephen F., Thomas L. Madden, Alejandro A. Schaffer,
Jinghui Zhang, Zheng Zhang, Webb Miller, and David J. Lipman (1997),
"Gapped BLAST and PSI-BLAST: a new generation of protein database search
programs", Nucleic Acids Res. 25:3389-3402.
Query=RESECO BLAST
UTILITY:\\r5840\pub\MolTox\blast\TRIMMED\MB2D\M2r02_NV.SEQ
(561 letters)
Database: nt
607,850 sequences; 1,816,255,750 total letters
Sequences producing significant alignments:                    Score      E gi|3228368|gb|K02061.|MUSRPL4A Mus musculus L32-4A pseudog . . .    565    e-159
gi|6981481|ref|NM 013226.1|| Rattus norvegicus ribosomal pr . . .   452    e-125
gi|3228368|gb|K02061.1|MUSRPL4A Mus musculus L32-4A pseudogene, complete seq
         Length = 1516
Score = 565 bits (285), Expect = e-159
 Identities = 360/384 (93%), Gaps = 5/384 (1%)
 Strand = Plus/Minus Query: SEQ ID NO: 1
       38       gcaggttttgtgattttatttaaacataaaacatgcacacaagccatctactcattttct   97
                |||||||||||||||||||||||||||||||||||||||||||||| ||||||||
Sbjct: SEQ ID NO: 2
       1094     gcaggttttgtgattttatttaaacataaaacatgcacacaagccatctattcattttct   1035

Query: 98      tcgctgcgtanccggcgttgggattggtgactctgatggccagctgtgctgctcttct   157
                |||||||||  |||||||||||||||||||||||||||||||||||||||||||||||
Sbjct: 1034    tcgctgcgtagcctggcgttgggattggtgactctgatggccagctgtgctgctcttct   975

Query: 158     acaatggcttttcagttcttanaggacacattgtgagcaatctcagcacagtaagatttg   217
                ||||||||||||| |||||||  |||||||||||||||||||||||||||||||||||||
Sbjct: 974     acaatggcttttcggttcttagaggacacattgtgagcaatctcagcacagtaagatttg   915

Query: 218     ttgcacatcagcagcacctccagctccttgacattgtggaccannaacttgcggaanccg   277
                ||||||||||||||||||||||||||||||||||||||||||  |||||||||||  |||
Sbjct: 914     ttgcacatcagcagcacctccagctccttgacattgtggaccaggaacttgcggaagccg   855

Query: 278     ctgggcagcatgtgcttggttttcttgttgctcccacaaccgaagtttnggcatcangat   337
                ||||||||||||||||||||||||||||||||||||| ||||||| | || |||||| |||
Sbjct: 854     ctgggcagcatgtgcttggttttcttgttgctcccataaccgatg-ttgggcatcaggat   796
```

TABLE 2-continued

```
Query: 338      ntggcccttgaaccttctcc-ccncctgttgtcnatgcctctgggtttccnc--atttcn  394
                ||||||||||||||||||| |  |||||||||| ||||||||||||||||| |    ||||
Sbjct: 795      ctggcccttgaaccttctccgcaccctgttgtcaatgcctctgggtttccgccagtttcg  736

Query: 395      cttaa-tttcccatatcggtctga  417
                |||||  ||||  |||||||||||
Sbjct: 735      cttaattttcacatatcggtctga  712
``` gi|6981481|ref|NM_013226.1|| *Rattus norvegicus* ribsml protein L32(Rpl32), mRNA
　　　　Length = 465
Score = 452 bits (228), Expect = e-125
Identities = 319/350 (91%), Gaps = 2/350 (0%)
Strand = Plus/Minus

```
Query: SEQ ID NO: 3
       38       gcaggttttgtgattttatttaaacataaaacatgcacacaagccatctactcattttct  97
                ||||  ||||||| ||||||||| ||||  ||||| ||||||||||||||| ||||| |||
Sbjct: SEQ ID NO: 4
       461      gcagttttgtggttttatttgaacacaaaacaggcacacaagccatctattcattctct  402

Query: 98       tcgctgcgtancctggcgttgggattggtgactctgatggccagctgtgctgctcttct  157
                |||||||||| ||||||||||||||||||||||||||||||||||||||||||||||||
Sbjct: 401      tcgctgcgtagcctggcgttgggattggtgactctgatggccagctgtgctgctcttct  342

Query: 158      acaatggcttttcagttcttanaggacacattgtgagcaatctcagcacagtaagatttg  217
                || |||||||||| ||||||| ||||||||||||||||||||||||||||||||||||||
Sbjct: 341      acgatggcttttcggttcttagaggacacattgtgagcaatctcagcacagtaagatttg  282

Query: 218      ttgcacatcagcagcacctccagctccttgacattgtggaccannaacttgcggaanccg  277
                ||||||||||||||||| ||||||||||||||||||||||||   ||||| ||||| |||
Sbjct: 281      ttgcacatcagcagcacttccagctccttgacattgtggaccagaaacttccggaagccg  222

Query: 278      ctgggcagcatgtgcttggttttcttgttgctcccacaaccgaagtttnggcatcangat  337
                || |||||||||||||||||||||||||||| ||||  |||| || || || ||||| |||
Sbjct: 221      ctaggcagcatgtgcttggttttcttgttactcccgtaacc-aatgttgggcatcaggat  163

Query: 338      ntgcccttgaaccttctcc-ccncctgttgtcnatgcctctgggtttcc  386
                |||||||||||| ||||||| |  |||||||||| |||||||||||||||
Sbjct: 162      ctggcccttgaatcttctccgcaccctgttgtcgatgcctctgggtttcc  113
```

Database: nt
 Posted date: Mar. 30, 2000 10:02 PM
Number of letters in database: 1,816,255,750
Number of sequences in database: 607,850
Lambda     K      H
   1.37    0.711  0.00
Gapped
Lambda     K      H
   1.37    0.711  4.94e-324
Matrix: blastn matrix:1-3
Gap Penalties: Existence: 5, Extension: 2
Number of Hits to DB: 420761
Number of Sequences: 607850
Number of extensions: 420761
Number of successful extensions: 34073
Number of sequences better than 10.0: 52
length of query: 561
length of database: 1,816,255,750
effective HSP length: 20
effective length of query: 541
effective length of database: 1,804,098,750
effective search space: 976017423750
effective search space used: 976017423750
T: 0
A: 0
X1: 6 (11.9 bits)
X2: 10 (19.8 bits)
S1: 12 (24.3 bits)
S2: 19 (38.2 bits)

Creating the First (Intermediate) Spreadsheet Files from the Search Results

In this step of the invention, the salient information in each HTML formatted search result file (Table 2.) is automatically reformatted and entered into a Microsoft Excel file. These files are the "search results Excel files". There will be one search result Excel file created for each HTML file originating from each sequence query. The Excel formatting allows the user to compare all database matches to a DNA fragment and to indicate which match, or matches, should be considered as the "best" for inclusion in the library's Excel file. Each search results Excel file is organized such that each row represents a single NCBI identity match. The highest scoring (best) matches are sorted to the top of the file. Hyperlinks into the NCBI database and to the HTML file are created at the time each file is created.

Table 3. below shows an example of an intermediate or search results Excel file. The intermediate or search results Excel file contains information about each NCBI database match to a single search sequence. The name of the file and its location as saved is contained at cell C1. The nucleotide sequence presented to NCBI for searching in its databases and the length of the sequence is given at cells C2 and C3, respectively. The first INDEX column A is numbered from the best to the worst sequence match HTML results. The USE IN LIB column allows the user to select a specific "best" sequence by placing any character in this box, otherwise the best match defaults to the first row of results. The third column contains the database (DB) searched. The fourth column (in bold) provides a hyperlink to the local HTML file (which is viewed using the default browser). The fifth column (bold) is a hyperlink address to the NCBI database record for accessing the data for the matched sequence information.

The remaining columns present the pertinent data automatically loaded from the HTML file returned by NCBI. These columns include the score, the "E" value probability, the date of the search, and the Description of the sequence. The last 12 remaining columns are data sets from the NCBI database match for the longest continuous sequence match. In these columns the Query is the unknown DNA sequence and the Target is the sequence matched in the NCBI database. These 12 columns include data on the $1^{st}$ Alignment score, the E value for the first alignment, Match ID's for the number of matched DNA sequence bases, Total ID's for the complete number of bases in the sequence identified, the number of Gaps in the query sequence compared to that in the database, a Query column (listed as default "plus" strand of sequence), a Subject column listing sequence match that is listed either as "plus" for the same sequence or "minus" for the antisense sequence match, the NCBI database Target Sequence Length, a column containing the position of Query DNA sequence minimum sequence, a column containing the position of Query maximum that matched the Subject sequence, and lastly, two columns showing the minimum and maximum sequence positions where the Query sequence has matched the subject sequence. Each row from number row six down in the file is information about a specific record in the NCBI database that matches the searched sequence.

TABLE 3

SEQ ID NO: 5

1 This File: \mricd-fs2\public\Molecular Toxicology\blast\EXCEL\MB2D\M2r02_NR.XLS
2 Sequence: ACAAGCTTTTTTTTTTTTTTTTTTTTTTTTTTTTTTGCAGGTTTTGTGATTTTATTTAAACATAAAACATGCACACAAGCCA TCTACTCATTTTCTTCGCTG
3 Length: 562'
4

| | A<br>Index | B<br>Use in Lib | C<br>DB | D<br>HTML File | E<br>GI | F<br>Score | G<br>Search Length | H<br>Search Date | I<br>Description | J<br>1st Alignment Score | K<br>E | L<br>Match ID's | M<br>Tot ID's |
|---|---|---|---|---|---|---|---|---|---|---|---|---|---|
| 5 | | | | | | | | | | | | | |
| 6 | 1 | | NR | M2r02_NR | 3228368 | 565 | 562 | Apr. 5, 2000 | Mus Musculus L32-4A pseudogene. complete sequence | 565 | e-159 | 360 | 384 |
| 7 | 2 | | NR | M2r02_NR | 6981481 | 452 | 562 | Apr. 5, 2000 | Rattus norvegicus ribosomal protein L32 (Rpl32), mRNA | 452 | e-125 | 319 | 350 |
| 8 | 3 | | NR | M2r02_NR | 57116 | 452 | 562 | Apr. 5, 2000 | Rat mRNA for ribosomal protein L32 | 452 | e-125 | 319 | 350 |
| 9 | 4 | | NR | M2r02_NR | 200778 | 434 | 562 | Apr. 5, 2000 | Mouse ribosomal protein L32' (rpL32') gene, complete cds | 434 | e-119 | 313 | 345 |
| 10 | 5 | | NR | M2r02_NR | 200773 | 434 | 562 | Apr. 5, 2000 | Mouse ribosomal protein L32' (L32') gene, complete cds | 434 | e-119 | 313 | 345 |
| 11 | 6 | | NR | M2r02_NR | 3152699 | 361 | 562 | Apr. 5, 2000 | Mus Musculus clone rpL32-5C ribosomal protein L32 (Rpl32) pseudogene complete sequence | 361 | 20CE-97 | 246 | 269 |

| | N<br>Gaps | O<br>Query | P<br>Subject | Q<br>Target Seq Length | R<br>Query Min | S<br>Query Max | T<br>Target Min | U<br>Target Max |
|---|---|---|---|---|---|---|---|---|
| 5 | | | | | | | | |
| 6 | 5 | Plus | Minus | 1516 | 38 | 417 | 712 | 1094 |
| 7 | 2 | Plus | Minus | 465 | 38 | 386 | 113 | 461 |
| 8 | 2 | Plus | Minus | 465 | 38 | 386 | 113 | 461 |
| 9 | 2 | Plus | Minus | 3663 | 43 | 386 | 1946 | 2289 |
| 10 | 2 | Plus | Minus | 901 | 43 | 386 | 361 | 704 |
| 11 | 0 | Plus | Minus | 750 | 43 | 311 | 334 | 602 |

Creating the Second (Library) Spreadsheet Files from the First Spreadsheet Files In this step of the invention, the final Excel Library files are created from the intermediate or search results Excel files. The "best" target identifications for each DNA isolate (the one at the top of the search results file) are compiled into a single Excel file for the subtraction library. The user selects a set of search results Excel files as input. The single output "library" file is created or updated with the information from these files. The user can review the search results by hyperlinking to the results in the intermediate Excel file, the HTML file or to the NCBI index citation of the sequence. The user can modify the selected description or add multiple descriptions, if needed, by placing any typed mark (such as an "X") in the third column of the search results "intermediate" Excel file (Table 3.) and recompiling the library. This appends the library file by placing all selected marked descriptions and the corresponding data into the subtraction library Excel file for all modified cDNA isolates.

Table 4. shows an example of a final Excel Library file. The Library file is designed to contain the best matches (or those selected as best matches from the Intermediate Excel File by the user) resulting from searches of the DNA sequences against each of the NCBI databases queried. The format of each row in the table is identical to the rows in the intermediate Excel files (see Table 3.). The only difference is that in the Library file, Column A contains a hyperlink to the Intermediate Excel File that contains all the matches to a single sequence or DNA isolate. In the intermediate Excel file, column A contains either a zero (0) to indicate no matching sequences found in the NCBI database or a one (1) to indicate that sequence matches were found. The Library file contains only the best (or user selected) match(s) for each of the many isolates that make up the DNA library.

TABLE 4

| 1 | A Index Row in Excel File | B Use in Lib | C DB | D HTML File | E GI | F Score | G Search Length | H Search Date | I Description | J 1st Alignment Score | K E |
|---|---|---|---|---|---|---|---|---|---|---|---|
| 2 | 0 | | EST | M2r01_EST | | | | Apr. 5, 2000 | <<<NO MATCHES IN NCBI DATABASE>>> | | |
| 3 | 0 | | NR | M2r01_NR | | | | Apr. 5, 2000 | <<<NO MATCHES IN NCBI DATABASE>>> | | |
| 4 | 0 | | EST | M2r02_EST | | | | Apr. 5, 2000 | <<<NO MATCHES IN NCBI DATABASE>>> | | |
| 5 | 1 | | NR | M2r02_NR | 3228368 | 565 | 562 | Apr. 5, 2000 | *Mus musculus* L32-4A pseudogene, complete sequence | 565 | e-159 |
| 6 | 1 | | EST | M2r03_EST | 1734682 | 593 | 522 | Apr. 5, 2000 | zo86a11r1 Stratagene ovarian cancer (#937219) *Homo sapiens* cDNA clone IMAGE 593756 5' similar to TR G893400 G892400 UMP-CMP KINASE. | 593 | e-167 |
| 7 | 1 | | NR | M2r03_NR | 6563219 | 759 | 522 | Apr. 5, 2000 | *Homo sapiens* UMP-CMP kinase mRNA, complete cds | 759 | 0 |
| 8 | 1 | | EST | M2r04_EST | 6590740 | 670 | 584 | Apr. 5, 2000 | 2820206 5prime NIH_MGC_7 *Homo sapiens* cDNA clone IMAGE 2820206 5' | 670 | 0 |
| 9 | 1 | | NR | M2r04_NR | 4758349 | 662 | 564 | Apr. 5, 2000 | *Homo sapiens* farnesyl-diphosphate farnesyltransferase 1 (FOFTI) mRNA | 662 | 0 |
| 10 | 1 | | EST | M2r05_EST | 1758572 | 575 | 293 | Apr. 5, 2000 | mt17e10r1 Soares mouse 3NbMS *Mus musculus* cDNA clone IMAGE 621354 5' similar to gb X92665 *M musculus* mRNA for ubiquitin-conjugating enzyme UbcM3 (MOUSE). | 575 | e-162 |
| 11 | 1 | | NR | M2r05_NR | 6678478 | 587 | 293 | Apr. 5, 2000 | *Mus musculus* ubiquitin conjugating enzyme 5 (Ubce5), mRNA | 587 | e-160 |

| | L Match ID's | M Tot ID's | N Gaps | O Query | P Subject | Q Target Seq Length | R Query Min | S Query Max | T Target Min | U Target Max |
|---|---|---|---|---|---|---|---|---|---|---|
| 1 | | | | | | | | | | |
| 2 | | | | | | | | | | |
| 3 | | | | | | | | | | |
| 4 | | | | | | | | | | |
| 5 | 360 | 384 | 5 | Plus | Minus | 1516 | 38 | 417 | 712 | 1094 |
| 6 | 401 | 423 | 11 | Plus | Minus | 471 | 26 | 441 | 52 | 470 |
| 7 | 429 | 441 | 4 | Plus | Minus | 1791 | 1 | 441 | 425 | 861 |
| 8 | 365 | 371 | 3 | Plus | Plus | 580 | 1 | 369 | 27 | 396 |
| 9 | 364 | 371 | 3 | Plus | Plus | 1649 | 1 | 369 | 13 | 382 |
| 10 | 290 | 290 | 0 | Plus | Plus | 608 | 1 | 290 | 140 | 429 |
| 11 | 289 | 290 | 0 | Plus | Plus | 1328 | 1 | 290 | 671 | 960 |

Preparing to Use the Subtraction Library Program

The raw sequence files are commonly output files from an automated DNA sequencer or a file generated from scanning an autoradiographic image of sequence gel. The raw sequence files are text files with each nucleic acid base being represented by a single ACSII character from the set (A, C, G, T, or N). After the last nucleotide in the sequence, a line feed character is expected. The sequence can be up to 5000 nucleotides long.

A vector file must be customized for a particular laboratory and selected prior to the trimming step. The vectors files are formatted using a six line, ASCII text format. Only the first contiguous string of letters on each line is read, so the remainder of each line can be used for annotations. Each line starts with a nucleotide sequence. An example vector file is presented below (SEQ ID NOS 6–11, respectively in order of appearance):

```
AGCGGCCGCCCGGGCAGGTC   // positive insertion orientation 5' adapter sequence ACCTCGGCCGCGACCACGCT   // positive insertion orientation 3' adapter sequence TTACTAGTGGATCCGAGCTCGGTACCAAGCTTC           // forward direction confirm
fragment 25 bases after 3' adapter AGCGTGGTCGCGGCCGAGGT   // negative insertion orientation 5' adapter sequence ACCTGCCCGGGCGGCCGCTC   // negative insertion orientation 3' adapter sequence CACACTGGCGGCCGCTCGAGCATGCATCTAGAG           // reverse direction confirm fragment
25 bases after 3' adapter.
```

In the vector file, the first two lines are used to hold the 5' and 3' adapter sequences that would be read from an insert that was positioned in a sense (or defined as "positive") orientation in the cloning vector. Lines four and five hold the 5' and 3' adapter sequences that would be read assuming an antisense (or defined as "negative") insertion orientation. The choice of the positive and negative orientation can be arbitrary, and the orientations only have meaning when related to the sense/antisense double-stranded DNA sequence orientation (as defined by the user or the subsequent search results). The third line holds a portion of cloning vector sequence, somewhat downstream of the 3' adapter that would be read when a plasmid is read in the defined forward sequencing direction. Line six holds a portion of the vector that would be read after the 3' adapter when reverse direction sequencing is done. As before, the choice of forward and reverse sequencing directions are arbitrary and have meaning only in relation to one another.

Using the Program

Figure 2:
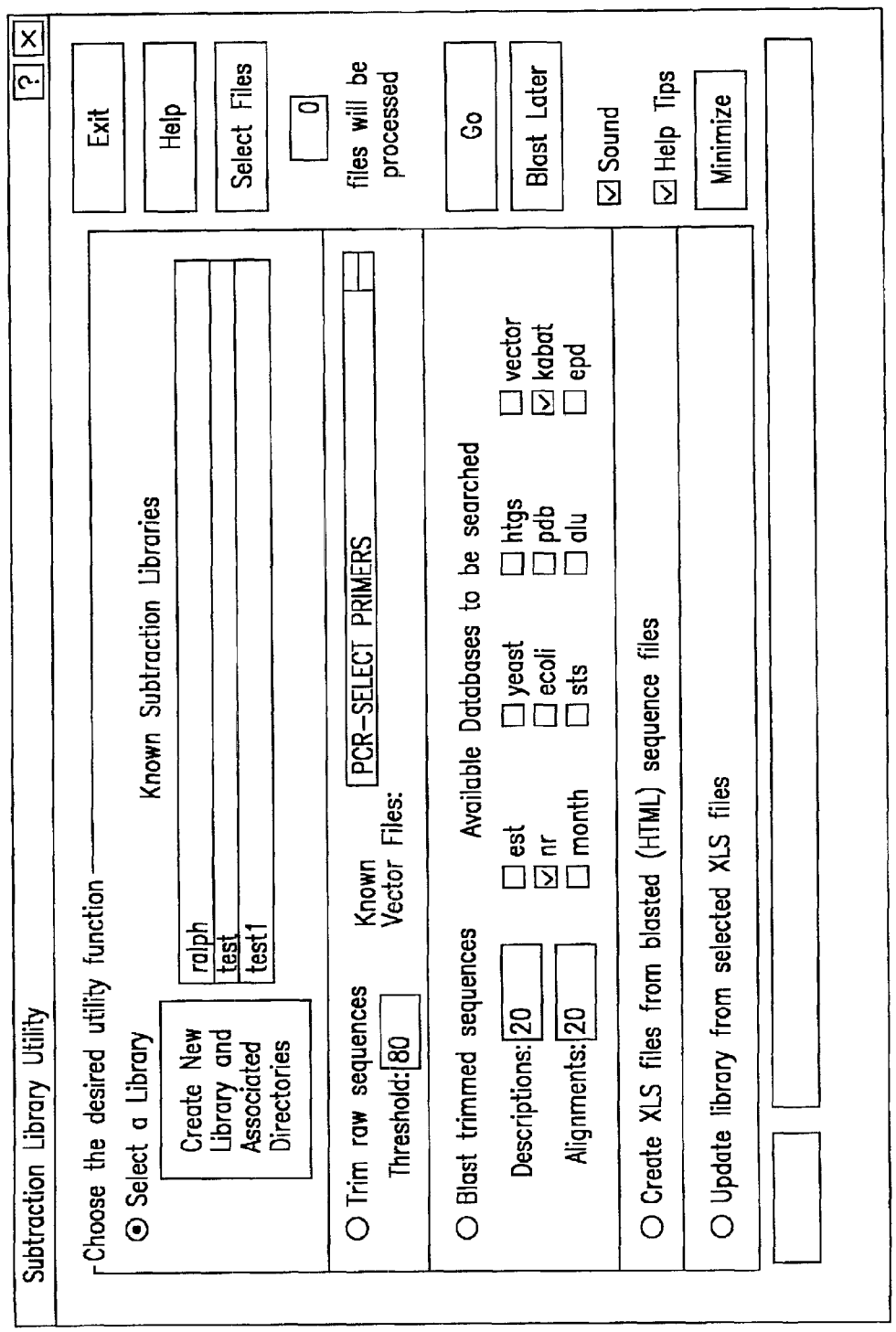
FIG. 2 shows a Main User Interface computer display.

Once started, the program presents the Main User Interface screen shown in FIG. 2. The left hand portion of the Main User Interface is organized into five sections. Each section is associated with one of the program modes of operation. The selector buttons along the left hand side indicate the program's current mode and allow the user to select a different mode. FIG. 2 shows the program in the "Select a Library" mode after three subtraction libraries have been defined. Certain fields are disabled in each program mode to limit the user to only compatible program choices. Each program mode is discussed below.

The "Select a Library" mode allows the user to select the library on which the program will operate by simply selecting it from the libraries named in the "Known Subtraction Libraries" list box. In FIG. 2, the subtraction library choices are "ralph", "test", and "test1". By clicking the "Create New Library and Associated Directories" button, the user directs the program to create all of the required directories and an empty subtraction library Excel file under a new subtraction library named by the user. These options are only available when the program is in this mode. Also, the selection or creation of a library is required for use of the subsequent program functions (i.e. trimming, searching, etc.).

In the "Trim Raw Sequences" mode, the user can select the vector file to be used from the "Known Vector Files" list box. This list box is filled with the names of all vector files found in the VECTORS subdirectory under the program's root directory. The user may also enter a value for the threshold percentage to be used when searching for the adapters or vector arm sequence in a raw nucleotide sequence. In this mode, the "Select Files" button in the right hand portion of the screen is activated to allow the user to select a set of raw sequence files to be trimmed. Once file selections have been made, the "Go" button on the right hand side of the screen will become activated. Clicking the "Go" button will display the Trimming Interface (see FIG. 3) and start the trimming procedures. The Trimming Interface is displayed for each selected raw sequence file to allow the user to specify the trim locations for each sequence. Trimmed sequences files containing only the saved sequence portion and trimming parameters files containing the trimming locations are created for each raw sequence. Trimmed sequence files are created using the original sequence naming convention (e.g. name.seq to name_nv.seq). When the trimming procedures are done, the Main User Interface is again displayed.

When the "Blast Trimmed Sequences" mode is selected, the "Descriptions", Alignments" and database selection checkboxes are activated. These fields allow the user to specify the maximum number of matching database records and the number of alignment displays returned from the NCBI data search for each of the database search requests. These database records and alignment displays are captured and saved to an individual HTML file. The check boxes allow the user to specify the NCBI databases to be included in the search. In this mode, the "Select Files" button in the right hand portion of the screen is activated. Clicking this button allows the user to select a set of trimmed sequence files to be submitted for database searching at the NCBI website. Database selections must be made prior to file selections. Once file selections have been made, the "Go" button and the "Blast Later" button on the right hand side of the screen will become activated. Clicking the "Go" button will immediately initiate the on-line NCBI connection for sequence identification. The lower boxes in the Main User Interface (FIG. 2) display the name of the active file to which data is being written and a running number of file bytes received in the HTML search results file for each individual query. The identification procedures result in an HTML formatted search results file for each combination of sequence and database searched. When the on-line identification procedures are complete, the Main User Interface is again displayed.

If the user chooses the "Blast Later" button rather than the "Go" button, the program allows the user to schedule a batch identification procedure to begin at some future time. If the batch identification is scheduled for a later time, the program exits. After batch identifications have been completed, the user must manually copy the created HTML files created from the library's directory under "C:\BLAST\HTML" to the proper directory under the root. The need for this manual copy is that the root linkage might not be available until the user logs back onto the computer. Thus, the computer (in the case of a network) which schedules the "Blast Later" event will initiate the later search and will receive the HTML files for storage.

In the "Create XLS files from blasted (HTML) sequence files" mode, the "Select Files" button in the right hand portion of the screen is activated. Clicking this button allows the user to select a set of multiple HTML files to be decoded into a corresponding set of Excel files. Once file selections have been made, the "Go" button on the right hand side of the screen will become activated. Clicking the "Go" button will start the file decoding procedures. When the procedures are done, the Main User Interface is again displayed.

In the "Update library from selected XLS files" mode, the "Select Files" button in the right hand portion of the screen is activated. Clicking this button allows the user to select a multiple set of Excel files to be incorporated into the Subtraction Library's Excel file. Only selected rows from each Excel file are incorporated into the Subtraction Library's file. In the absence of a specific user indicator (such as an "X" or "a user's initials" in row three of the intermediate Excel file) that defines which rows to be used, only the top row (best match) from each Excel file is used. Once file selections have been made, the "Go" button on the right hand side of the screen will become activated. Clicking the "Go" button will start the compilation procedures. When the procedure is done, the Main User Interface is again displayed.

Across the bottom of the Main User Interface (FIG. 2), there are two display fields that present feedback information for the user during the NCBI database searching. The smaller field on the left presents the Internet Protocol (IP) address at which the NCBI server was found. The larger field is used to display the status and name of the HTML input file that is currently being filled with results returned from the NCBI search engine.

User Controls

At the right hand side of the Main User Interface (FIG. 2) a number of buttons are provided to allow the user to control the program operations for the selected program mode. The "Exit" button causes the program to shut down in an orderly fashion regardless of the current operation. The "Help" button launches a help system. The "Select Files" button allows the user to specify a set of input files to be processed during the "Trim raw sequences" mode, the "Blast trimmed sequences" mode, the "Create XLS files from blasted (HTML) sequences files" mode or the "Update library from selected XLS files."

In the "Blast trimmed sequences" mode, the check boxes specifying the NCBI databases to be searched should be set prior to pressing the "Select Files" button. The input files must all be selected from a single directory. Normally, this directory will belong to the set of directories associated with the currently selected subtraction library, but the input files may be pulled from any location. As a convenience, the file selection window is positioned by default, depending on the program mode, to the appropriate directory associated with the currently selected subtraction library. Note that the user has no control over where the output files created by the processing are placed. Output files are put into the appropriate directory created as part of a user-named library associated with the currently selected subtraction library.

The "files will be processed" field displays the number of output files that will be produced by the currently requested operation. Usually, this number will be equal to the number of files selected as input. In the "Blast trimmed sequences" mode, however, each selected input file may be processed up to twelve times, depending on the designated NCBI databases to be searched. Each database search of a trimmed sequence will create an output file.

Pressing the "Go" button starts the processing of the selected files. The "Go" button becomes enabled after a file selection has been done. The processing that is performed depends upon the current program mode. The operations are summarized below for each program mode where input files are selected:

"Trim Raw Sequences" Mode

The trimming interface screen (FIG. 3) is presented, in turn, for each selected input file. The interface allows the user to specify the portion of the sequenced plasmid that is to be saved for identification at NCBI. The trimmed sequence is stored under the original sequence name appended with_nv after the given sequence name (i.e. name-nv.seq) in the subdirectory associated with the currently selected subtraction library located under the TRIMMED directory.

"Blast Trimmed Sequences" Mode

For each selected trimmed sequence file and each specified database, a request for the NCBI server is prepared and sent. The user must have Internet access or the connection will fail. The program waits for the search results to be returned from one request before the next request is sent to NCBI. Audio and visual feedback is provided to inform the user that the program is working. The results are stored in HTML format in the subdirectory associated with the currently selected subtraction library under the HTML directory.

"Create XLS Files from Blasted (HTML) Sequence Files" Mode

For each selected HTML input file, the program opens a "Blank.xls" file, fills it with information parsed from the HTML file, and saves the filled XLS file under an appropriate sequence name in the subdirectory associated with the currently selected subtraction library under the EXCEL directory.

"Update Library from Selected XLS Files" Mode

For the currently selected subtraction library, the program opens the subtraction library's XLS file. Each of the selected input XLS files (one created from each HTML file) are then opened, in turn, and the "best" identification from each is copied into the subtraction library file. By default, the "best" match is determined by the highest matching score from the NCBI data search received in the HTML file. If the user wishes to specify a different identification as the best match or include multiple identifications, the user can hyperlink to the intermediate Excel file and place a mark in column 3 of the file and rerun the "Update library" mode. This action will append all newly user indexed sequence match entries to the bottom of the spreadsheet. If the user would prefer to overwrite the data, the complete data set can be highlighted and deleted and the library then recompiled. If the subtraction library already existed, any duplicate identifications are overwritten with fresh data. When updating is completed, the subtraction library XLS file is saved under the library's name in the LIBRARY directory.

When the program is in "Blast trimmed sequences" mode and a set of input files has been selected, the "Blast Later" button is enabled at the same time as the "Go" button. Whereas the "Go" feature will start immediate processing of the selected files, the "Blast Later" feature will allow the user to postpone the NCBI searching until some specified time up to 24 hours later. This feature could be used, for instance, to submit the search requests at a time when the NCBI server is not expected to be busy. The user specifies the starting hour and minute for the operations to begin. If the time specified is earlier than the current time, the request is submitted the next day. The user may also choose to use the operating system to manually schedule the request, rather than letting it be scheduled automatically. When this is done, a batch file is created in the "C:\BLAST" directory that will perform the search when it is run. This might be done, for instance, if the user wished to schedule the batch job to run several days hence. The manner in which a batch job is scheduled varies with the computer operating system.

If the "Sound" box is checked, a tone is produced at the beginning of the processing of each file. When a search request has been sent to NCBI, a tone is also presented each time the program checks for returned results. These tones, along with the status indicators, inform the user that the program is still working and has not crashed. If the user wishes, the audio tones can be disabled by not checking the "Sound" box.

If the "Help Tips" box is checked, balloon type text appears when the cursor is left in positions over an active item on the interface. The displayed text provides a short description of the purpose for the item.

The "Select a Library" mode selector is used to place the program into "Select a Library" mode. In this mode, the user may specify the "currently selected" subtraction library by highlighting its name in the "Known Subtraction Libraries" list. The user may also create a new subtraction library and its associated subdirectories by pressing the "Create New Library and Associated Directories" button. The program operates on files belonging to a single, currently selected, subtraction library. Each subtraction library known to the program will have an associated Excel formatted XLS file in the LIBRARY directory and associated subdirectories under each of the SEQUENCE, TRIMMED, TRIMPARS, HTML, and EXCEL directories. The subtraction library with which the user wishes to work is selected from those presented in this list of previously created libraries. The library whose name is highlighted on the list becomes the "currently selected" subtraction library. When the program is first installed, there are no subtraction libraries present, so this list will be empty. As the user creates new subtraction libraries, using the "Create New Library and Associated Directories" button, more entries will be available on this list.

The "Create New Library and Associated Directories" button allows the user to make a new subtraction library known to the program. When this button is pressed, the user is asked to specify the name of the new subtraction library. The user must type the desired name for the new subtraction library into the space provided and press the "OK" button. If the name has not previously been entered, it is used to create a new, blank, subtraction library XLS file in the LIBRARY directory and to create all required subdirectories. The new name will then appear on the "Known Subtraction Libraries" list. The user may press the "Cancel" button to end the request with no actions taken.

Activating the "Trim Raw Sequences" selector places the program in "Trim raw sequences" mode. In this mode, unlike the other processing modes, the user is required to make decisions as part of the processing of the selected files. Settings for two parameters that are used in the automated trimming feature available in this mode may be specified prior to initiating the processing. The user may specify the name of the vector file and the threshold percentage level for finding a sequence match in the trimmed sequence.

Automated trimming of the raw sequence files is based upon finding the nucleotide sequences of known adapters in the raw sequence. These adapters are added for polymerase manipulation to the ends of the cDNA fragment before it was inserted into a cloning vector and then sequenced. In the raw sequences output from the DNA sequencer, the portion between these known sequences is used as the fragment-of-interest to be identified. The adapter/vector sequences to be used are read from "vector" files stored in the VECTORS directory. The user will create a vector file to be used and place it, manually, in the VECTORS directory prior to trimming sequences from a subtraction library. The "Known Vector Files" list is filled with the names of all vector files in the VECTORS directory. The user specifies the adapter set to be used by highlighting the file's name in this list.

The "Threshold" field entry is used to display the current threshold percentage level to be used when the automated trimming feature is employed. The automatic selection of trimming positions is based upon how well adapter/vector sequences match the raw sequence at specified locations. The scoring is based upon a weighted percentage of matching nucleotides. Mismatched nucleotides are assigned a weight of zero. Matching nucleotides are assigned a weight of two. A nucleotide paired against an "undetermined", N, nucleotide is assigned a weight of one. The score for the match at a position ranges from 0 to 100 percent. For a particular adapter, if a trimming position cannot be found that results in a score at least as high as the threshold percentage, the "automated" position used is swept to the proper end of the raw sequence (to the start for 5' adapters; to the end for 3' adapters). The user may enter an integer from 0 to 101 into the threshold field. Since the maximum possible matching score is 100, specifying 101 forces the automatic search to place the entire raw sequence into the sequence confirmation file. The value is set to 80 by default. No trimming is done or trimmed sequence file created without a user confirmation. The automatic trimming merely suggests trimming locations. The user may adjust these locations as desired (using scroll bars) before confirming the trim. The trimming can subsequently be changed, since the raw sequences are not altered in any way.

The "Trimming Interface" Screen

Once the parameters have been specified, and a set of files to be trimmed has been selected using the "Select Files" button, the "Go" button is activated to allow the user to start the processing of the files. For each file to be trimmed, the "Trimming Interface" (FIG. 3) is displayed. Using this interface, the user specifies or confirms the locations used to mark the beginning and end of the fragment-of-interest portion of a raw sequence. This is the portion that represents the nucleotides in a fragment of a cDNA (from mRNA) molecule in the subtraction library.

The main function of the Trimming Interface screen is to allow the user to specify (using the scroll bars) the starting and ending locations of the nucleotides representing the DNA insert fragment-of-interest. After the trimming scroll bars have been set, trimming is performed by pressing the "Apply" button to trim the raw sequence on either side of the fragment-of-interest.

The middle large window portion 10 of the Trimming Interface (FIG. 3) shows the raw sequence. The cDNA fragment-of-interest, which corresponds to the fragment of cDNA (from mRNA) in the subtraction library, is the sequence located between the 5' adapter section 12 and the 3' adapter section 14. Portions of the sequence that match or differ from another sequence are color-coded for ease of visual detection. The fragment-of-interest may be shown in black, except for any unidentified nucleotides. Unidentified nucleotides are represented by the letter "N". The "N" letters may be highlighted by showing them in a color other than black, for example, a magenta color. The portions of the raw sequence that will be trimmed are the 5' adapter section 12, the 3' adapter section 14 and any sequence occurring before the 5' adapter section 12 or after the 3' adapter section 14.

Figure 3:
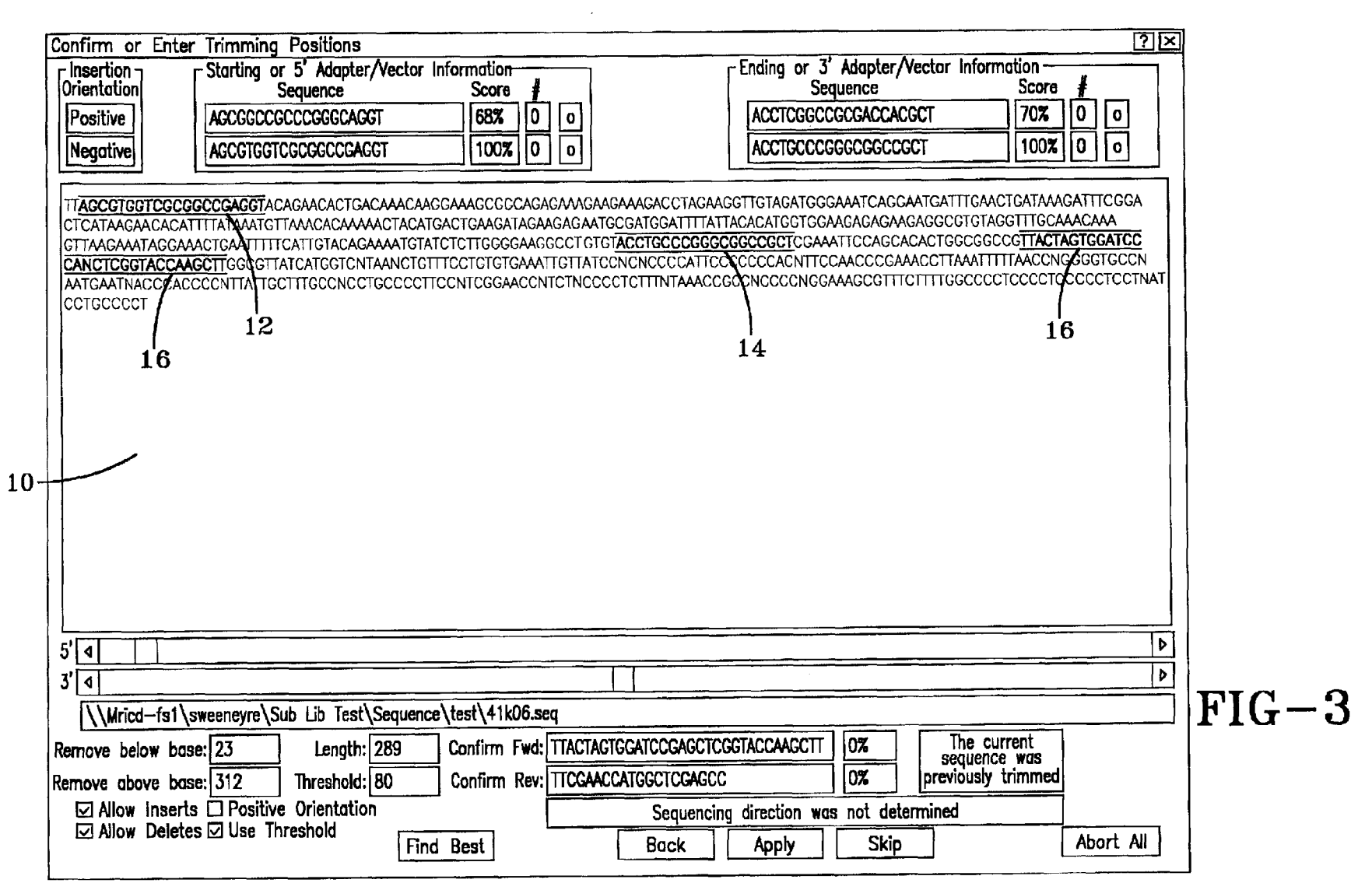

The portions of the raw sequence that will be trimmed may be shown in either blue (negative inserts) or red (positive inserts), except for additional highlighting used on the 5' and 3' adapter sections 12 and 14. Another color, such as green, may be used to indicate if the trimming function determines that a nucleotide has been erroneously inserted into the raw sequence by the DNA sequencer. The raw sequence nucleotides that are being compared against the 5' and 3' adapter nucleotides are shown in FIG. 3 in the boxes 12 and 14, respectively. The raw sequence nucleotides 12 and 14 may be indicated graphically with yellow bars drawn above and below them. If the corresponding nucleotides match, the raw sequence nucleotides 12 and 14 may also be drawn in yellow.

The 5' and 3' trimming locations can be adjusted by the user with the two scroll bars displayed under the raw sequence display area 10. In FIG. 3, the adapters nucleotides all match the raw sequence, so both the 5' adapter section 12 and the 3' adapter section 14 would be drawn completely in yellow. Trimming of the raw sequence occurs at the trailing (right) edge of the 5' adapter 12 and the leading (left) edge of the 3' adapter 14. Nucleotides in the raw sequence that do not match the corresponding nucleotide in the adapter may be drawn in the trim color for the determined insertion orientation (for example: positive is red, negative is blue). Any nucleotide to the left of the 5' section 12 is also drawn in the trim color. Any nucleotide to the right of the 3' section 14 is drawn in the trim color, unless it falls in the confirmation section.

As an additional check, sections of the cloning vector, taken from either side of the insertion location, are compared against the raw sequence. Depending on the sequencing direction chosen by the user, one of these confirmation vector sequences should appear downstream from the 3' adapter 14 in the raw sequence, if the complete insert has been sequenced. The presence of such a portion of the cloning vector provides confidence that the DNA sequencing reaction and gel run was still sufficiently strong for accurate identification of a DNA sequence location past the fragment-of-interest and that the 3' adapter sequence match was not found by chance within the sequence of interest. The position and matching of the nucleotides in the confirmation section may be displayed in a white color. Both confirmation sequences are compared against all positions downstream of the 3' adapter 14. The best match is used to determine both the location of the confirmation section in the raw sequence and the direction in which sequencing was performed. The position of the confirmation sequences cannot be adjusted by the user during the sequence trimming. However, the position of the confirmation sequences can be selected by creating a new vector file or by choosing an appropriate section in the adapters file in the Vectors subdirectory. It is best to have the confirmation sequence within 16–20 bases after the end the 3' adaptor 14.

The Trimming Operation

Unlike the other program modes, the user provides the active step in the trimming operations. When the trimming positions are displayed, the user can press one of a number of buttons to carry out a desired function. The trimming positions can be set manually using a set of horizontal scroll bars.

The color coded display is designed to provide the user with a graphical description of how well the 5' and 3' adapters 12 and 14 match the raw sequence at the currently selected 5' and 3' adapter locations. These locations are automatically placed by the program within the sequence at the best matching sequence or can be controlled using the 5' and 3' adapter position scroll bars located just below the raw sequence display area 10. Since raw sequence trimming occurs just to the right of the 5' adapter (reference numeral) 12 and just to the left of the 3' adapter (reference numeral) 14, the scroll bars actually set the trimming locations. The user is free to set the scroll bars to any desired positions and, therefore, has total control over how the raw sequences are trimmed. As the scroll bars are moved, most of the information on the interface will change to reflect the scoring that results given the updated trimming locations. An automated trimming feature (discussed later) helps the user adjust the scroll bars to the proper trimming locations. Once the scroll bars have been adjusted as desired, the user must press the "Apply" button to carry out the trimming of the sequence and progress to the next sequence. Or, the user may choose one of five control buttons discussed next.

When the "Find Best" button is pressed, an automated trimming feature is used to match the 5' and 3' adapters at all possible trimming locations while assuming either positive or negative insertion orientations. The highest score for the 5' adapters is used to determine both the 5' trimming location and the insertion orientation. The best 3' adapter score in that orientation is used to determine the 3' trimming location. At each possible location after the 3' adapter sequence, the two confirmation sequences are matched against the raw sequence. The highest score is used to determine both the locations of the confirmation sequence and the sequencing direction. The display is updated to reflect these "Best" locations. The user may press the "Find Best" button at any time to return to the best locations. If the trimming locations for a raw sequence have not previously been set, this feature is automatically run when the trimming interface is opened and a sequence from the selected raw sequence file is displayed.

When the "Apply" button is pressed, the current trimming locations are applied to the raw sequence file being trimmed. The trimmed sequence is stored in a trimmed sequence file of the same base name with the string "_NV" appended. The "NV" means "No Vector". A trimming parameters file is created in the appropriate TRIMPARS subdirectory to preserve the current trimming locations. The program then proceeds to the next file in the selected set of raw sequence files.

If the user is currently trimming the second or any subsequent file in the set of raw sequence files, the "Back" button is activated to allow the user to return to the trimming of the previous file. The trimming locations of the current file remain unaltered. The location of the previously accepted adapters for the trimmed sequence is shown from the stored information in the trim parameters subdirectory labeled "TRIMPARS".

Pressing the "SKIP" button aborts the trimming of the current file and progresses to the trimming of the next file in the selected set of raw sequence files. If the current file has been previously trimmed, the trimming locations are unaltered. If the sequence has not been trimmed previously, no_NV file will be created for further use in the subsequent sequence identification and information archival steps.

If the user has selected a large set of raw sequence files and decides to stop trimming them after trimming has been started, skipping over each of the remaining files can be burdensome. The "Abort All" button allows the user to cancel the trimming of the current and all of the remaining raw sequence files that were selected for trimming.

Automatic trimming is activated by pressing the "Find Best" button. Most of the fields and buttons on the trimming interface screen are devoted to controlling the parameters used for automatic trimming, or for displaying the scores associated with the current trimming locations. These scores are used to determine the best trimming locations.

Because there are two possible orientations for incorporation of the cDNA insert into the cloning vector using certain cloning techniques, adapter matching of each sequence in both orientations must be considered. For the user's information, the 5' and 3' adapter sequences are presented, as they would appear in the raw sequence for both insertion orientations, at the top of the Trimming Interface screen in the 5' and 3' adapter information areas. The upper fields in each area correspond to the positive insertion orientation. The lower fields correspond to the negative insertion orientation. The highest score found when matching the two 5' adapters to the raw sequence is used to determine the insertion orientation. The user may override the determined insertion orientation using the "Positive Orientation" checkbox shown at the bottom left portion of the interface. The current orientation is indicated by both that checkbox and the highlighting of the "Insertion Orientation" fields at the upper left of the interface. Note that the sense of the insertion is arbitrary, and is fixed by the vector file.

The 5' and 3' adapter information areas are organized into two sets of three field displays labeled "Sequence", "Score" and "#" and a single control button (shown to the right of each set). The upper set of three field displays is associated with the positive insertion orientation and the bottom set of three field displays is associated with the negative insertion orientation. The "Sequence" field shows the nucleotide sequence, read from the appropriate line in the vector file that is being used. The "Score" field shows the score (100% is perfect match) that results from matching the related adapter to the raw sequence at the current trim position. The "#" field shows the number of trimming locations which result in scores equivalent to the one being shown for the current trim position. The "o" button shown to the right of each set of fields, when enabled, will adjust the related trimming position to the next location that produces an equivalent matching score, if found, for the adapter sequence.

The sequencing is done toward the inserted fragment starting from one vector sequence "arm" position where insert DNA was ligated into the cloning vector. A technician using an oligonucleic DNA primer matching either side of the known DNA adapter or vector that incorporates the insert can do the sequencing. One of the sequencing directions can (arbitrarily) be chosen to be the forward direction. Two vector confirmation sequences should be taken from the nucleotides in the cloning vector at a distance of approximately 16–30 nucleotides away from either side of the inserted adapters and entered into the vector file in the appropriate lines. The confirmation information area of the Trimming Interface, located below the scroll bars to the right, is used to present the confirmation sequences used for each direction and the highest score that could be achieved by matching each against all positions downstream of the current 3' adapter. The sequence with the higher score is used to determine the sequencing direction used. The determined direction is presented in the field at the bottom of the confirmation information area. The confirmation sequence is shown in FIG. 3 as the plasmid vector sequence denoted by reference numeral 16, again giving further information on known sequence regions for assuring successful raw sequence trimming.

The scoring algorithm uses a method wherein a nucleotide paired with a matching nucleotide is assigned a weight of 2, a nucleotide paired with an unidentified nucleotide is assigned a weight of 1, and a nucleotide paired with a mismatched nucleotide is assigned a weight of 0. The score is computed as a percentage of the highest score possible for the adapter sequence. A score is computed for a particular adapter (or confirmation) sequence at a particular position in the raw sequence. When the "best" locations for trimming are sought, both 5' adapters are compared against every location in the raw sequence. The insertion orientation is set according to the orientation associated with the higher scoring 5' adapter. The 5' trimming location is the position where that 5' adapter gave the highest score. The associated 3' adapter is then compared against all positions downstream of the selected 5' adapter. The position giving the highest score is then used as the 3' trimming location. Finally, both confirmation sequences are compared against the raw sequence at all positions downstream of the selected 3' adapter location. The highest score found is used to determine both the confirmation location and the sequencing direction.

The threshold value entered while in "vector mode" on the Main User Interface screen is also used in the automatic location of the best adapter positions. This threshold value, which is a scoring percentage, indicates the minimum match score that will be accepted in an automated position search. If a position cannot be found that meets the threshold criteria, then the offending adapter is positioned past the appropriate end of the raw sequence. For instance, if no position can be found that matches the 3' adapter suitably, the 3' trim location is moved past the end of the raw sequence. This will result in no 3' trimming of the raw sequence. This case is by far the most common and occurs when the length of the inserted fragment is greater than the number of nucleotides that can be sequenced beyond the reliability of the sequencer reactions. The threshold feature can be disabled by removing the check in the box labeled "Use Threshold" check box at the lower left portion of the Trimming Interface.

The user may allow single nucleotide insertions in the raw sequence to be considered in the match scoring by setting the "Allow Inserts" check box in the lower left portion of the Trimming Interface. Similarly, the user can allow the program to consider single deletions (a nucleotide erroneously missed by the DNA sequencer) by setting the "Allow Deletes" check box. When these check boxes are set, the scoring algorithm will additionally allow for a single nucleotide insertion or deletion in the raw sequence. A graphical presentation of the incorporation of a single insertion or deletion is given in the trimming display. If a nucleotide is determined to have been erroneously inserted into the raw sequence based on the adapter or vector sequence in the chosen vectors file, then the suspected nucleotide is displayed is green, and the sequence confirmation lines drawn above and below the string of nucleotides are omitted. If a nucleotide is determined to have been erroneously deleted from the raw sequence, then a break is displayed in the raw sequence display at the position where the suspected nucleotide would have appeared.

There are three fields at the lower left portion of the Trimming Interface which relate to the length of the trimmed sequences that would result if trimming were done at the currently set trimming locations. The "Remove below base" and "Remove above base" fields give the nucleotide numbers in the raw sequence (starting from 1) where the actual trimming will take place. The "Length" field shows the length, in nucleotides, of the trimmed sequence. The "Threshold" field shows the threshold value of required percentage sequence match to be found and displayed. The threshold value was set on the Main User Interface screen. A field to the right of this area indicates whether or not the current sequence has been previously trimmed. A field just below the scroll bars shows the full filename of the raw sequence currently being trimmed, including its subdirectory location.

Using the "Blast Trimmed Sequences" Mode

Clicking the "Blast trimmed sequences" mode selector on the Main User Interface screen (FIG. 2) places the program into "Blast trimmed sequences" mode. This mode allows the user to submit trimmed sequences to be searched against NCBI databases for the purpose of identifying the sequence. "Blasting" is a term used to describe the process of submitting a sequence of nucleotides (a search string) to NCBI's Basic Local Alignment Search Tool (BLAST) program, for it to search against a number of databases maintained by that facility. The identities of many known nucleotide sequences are stored in the NCBI databases along with the sequence strings. When a database is searched using the BLAST program, the submitted search string is compared against all of the sequences known to the database and a set of record identifiers is returned for which the search string at least partially matched the sequence in the record. The identification information presented in the returned records also allows the user to identify if the same or a similar sequence has been donated to the database and the name of the protein identities to which the submitted string might belong. The results returned from the search of each NCBI database are stored in an HTML formatted file that may be viewed with a web browser. One HTML file is created for each trimmed sequence searched against each database. For examples, if the user selects five trimmed sequences and specifies that three databases should be searched, there will be fifteen HTML files created. The HTML files can be processed into Excel spreadsheet files using the "Create XLS files from blasted (HTML) sequence files" mode, which would result in the creation of fifteen intermediate Excel files and, subsequently, one Excel Library file having fifteen lines of text.

The program uses a web-based interface into the NCBI server so that access can be obtained from behind a network firewall without intervention by network administrators. This is the same access route used by the popular web browsers. When the user starts the process of blasting a set of trimmed sequence files, the program will process each file sequentially. The processing of each file includes formatting a search request, connecting to the server; submitting the request; receiving the HTML formatted data that is returned and saving it to disk; and disconnecting from the server. This automated process contains features that allow an automated recovery after unexpected connection failures, loss of the data stream or failure of the NCBI site. The user would normally minimize the program during this processing and work on some other task. The program title is modified to display progress information when the program is minimized.

In the "Blast trimmed sequences" mode, the "Select Files" button is activated to enable the user to choose the set of trimmed sequences files to be identified by blasting on the NCBI server. There are several fields (discussed in the following sections) that allow the user to specify parameters to be used by NCBI's search engine.

When a trimmed sequence is searched against a database, the sequence is compared to sequence stored in each record of the database. If there is a suitable match somewhere in the stored sequence, the database record is thought of as a "hit". The trimmed sequence may match sequences in many database records. Descriptive information about each matched database record is returned from the search. The best matches are returned first. The user may limit the number of database hits returned by entering the desired maximum number in the "Descriptons" field on the Main User Interface.

Detailed information about each matched database record (including a text representation of the areas where the two sequences match) is returned from the search is the form of "alignments". The returned alignments correspond to the returned descriptions, with the best matches being returned first. The user may limit the number of database alignments that are returned by entering the desired maximum number in the "Alignments" field on the Main User Interface.

There are many databases maintained on the NCBI server. The user may choose the databases to search by using the "Available Databases to be searched" check boxes on the Main User Interface. A separate set of HTML formatted results will be returned for each database chosen. The non-repetitive (NR) and the expressed sequence tag (EST) databases are commonly searched. As of November 2000, there were 20 databases maintained by NCBI. The program allows the user to specify up to 12 of those databases. The databases that are available are:

| | |
|---|---|
| ALU | Search ALU repeats |
| ECOLI | Search *E. coli* Genomic sequences |
| EPD | Search Eukaryotic Promoter Database |
| EST | Search the Expressed Sequence Tags (EST) database |
| HTGS | Search Unfinished High Throughput Gene Screening Data |
| KABAT | Search Sequences of Immunological Interest |
| MONTH | Search only new records entered for the current month |
| NR | Search non-repetitive records |
| PDB | Search the Protein Data Bank (PDB) |
| STS | Search the Sequence Tagged Sites (STS) database |
| VECTOR | Search Known Vector Sequences |
| YEAST | Search Yeast Genome/Expressed Sequences |

Once the user has specified the search parameters and selected a set of files, the "Go" and the "Blast Later" buttons are activated. The "Go" button is used to start searching immediately and to return to the program when all files have been processed. Once the processing of all selected files is complete, the program returns to the Main User Interface screen. The interaction with the NCBI website can be slow, particularly at times when many users are accessing the site. Although the user can minimize the program and work on other tasks, it is possible to submit the search requests at a time when the NCBI server is not being heavily used. The "Blast Later" button is used to allow the user to schedule the searching to begin at some later time as a batch process. When the "Blast Later" option is used, the program will automatically close after the batch operations are scheduled.

When the user presses the "Blast Later" button, an "Enter Time to Start Blasting Sequences" interface is presented. The user selects the military style (i.e, twenty four hour clock) hour and minute at which the blasting should begin. Pressing "OK" commits to the batch processing. Pressing "Cancel" cancels the request. If the specified time is earlier than the current time of day, then the blasting will begin at the specified time the next day. This allows delaying the start for up to 24 hours. Once the start time has been selected, the program will create a batch file that can be scheduled to execute at a specific time. This feature is intended to allow the blasting of files to be done at times when the NCBI server is not busy. The actual scheduling of the batch execution can be done either automatically or manually using the features available in the computer operating system. By default, the scheduling is done automatically. The user can disable this feature by setting the "I will schedule the start time using the operating system" check box on the Start time interface screen.

Using the "Create XLS Files from Blasted (HTML) Sequence Files" Mode

In the "Create XLS files from blasted (HTML) sequence files" mode, the user may select a set of HTML files that will be converted into Microsoft Excel files. The Excel files are designed to present the information parsed from the HTML files in an orderly manner, and to create hyperlinks into both the component HTML files and the NCBI database records. These hyperlinks allow the user to review identity and other information about a particular piece of sequence data. The "Select Files" button is used to specify which HTML files will be converted. The "Go" button starts the conversion process. Conversion of each HTML file results in an XLS file being produced. After the conversions, the user is returned to the Main User Interface screen. Each created XLS file is organized using one row for each match to the submitted sequence such that the "best" matches (sequence identifications with the most confidence) are presented at the top rows of the file. Selected rows from the XLS files are compiled into a single, subtraction library XLS file using the "Update library from selected XLS files" mode. The user may indicate which rows should be included in the associated subtraction library XLS file by placing symbols in the "Use in Lib" column of the desired rows in each XLS file.

Using "Update Library from Selected XLS Files" Mode

This program mode is used to compile the indicated rows from each search result XLS file into a single Microsoft Excel file that is referred to as the subtraction library XLS file. The "Select Files" button allows the user to specify the search results XLS files that are to be used in the update. After a set of files has been selected, the "Go" button is used to perform the update of the subtraction library XLS file. During the update process, information from marked rows in each search result XLS file are compared to each row in the subtraction library XLS file. If a similar row in the subtraction library file is not found, a new row of information is appended to the end of the subtraction library XLS file. Otherwise, the information is used to replace the similar row in the subtraction library file. If the user has not specifically marked rows in an XLS file for inclusion into the library file, then the highest scoring match row is used.

The purpose of the subtraction library file is to present the "best" and most current sequence identifications for each DNA or cDNA (mRNA) fragment that were isolated in the library technique. In the case of the subtraction library technique, viewing the best identification data for each isolate will enable the researcher to ascertain which mRNA molecules have been up (or down) regulated and aid in hypothesis generation. Hyperlinks are included in the final subtraction library file so that the user may quickly review the best identifications for a single isolate, the alignment of any single database match, or related information in the NCBI databases. The immediate link to specific data at the NCBI includes a multitude of NCBI linkages to such information as the position of the sequence in the genome, information about the present knowledge and function of the protein, as well as an immediate gateway to PUBMED literature databases. Also, this condensed DNA data identity format allows the use of the Excel sorting and the storage of data in electronic form.

While the invention has been described with reference to certain preferred embodiments, numerous changes, alterations and modifications to the described embodiments are possible without departing from the spirit and scope of the invention as defined in the appended claims, and equivalents thereof.

What is claimed is:

1. A method of obtaining and organizing information about a plurality of unknown raw nucleic acid sequences, comprising:
   a) creating a directory of files in a computer, for storing information related to the plurality of unknown raw nucleic acid sequences;
   b) inputting the plurality of unknown raw nucleic acid sequences into the computer;
   c) automatically determining trimming locations of each unknown raw nucleic acid sequence using a best match type scoring algorithm which, during each scoring operation, assigns a nucleotide paired with a matching nucleotide a highest value, assigns a nucleotide paired with an unidentified nucleotide an intermediate value and assigns a nucleotide paired with a mismatched nucleotide a lowest value and which, during each scoring operation, allows either a single nucleotide insertion or a single nucleotide deletion in the unknown raw nucleic acid sequence, the scoring algorithm first comparing a known positive 5' adapter sequence and a known negative 5' adapter sequence to the raw nucleic acid sequence and assigning a 5' trimming location to a position in the unknown raw nucleic acid sequence having the highest score and determining an insertion orientation according to the higher scoring of the known positive and negative 5' adapter sequences, then comparing a known 3' adapter sequence having a same orientation as the higher scoring known 5' adapter sequence to the unknown raw nucleic acid sequence and assigning a 3' trimming location to a position in the unknown raw nucleic acid sequence having the highest score, then comparing a known positive confirmation sequence and a known negative confirmation sequence to the raw nucleic acid sequence and assigning a confirmation sequence location to a position in the unknown raw nucleic acid sequence having the highest score and determining a sequencing direction according to the higher scoring of the known positive and negative confirmation sequences, and then trimming each of the plurality of unknown raw nucleic acid sequences to obtain a respective plurality of trimmed unknown nucleic acid sequences;
   d) submitting each of the plurality of trimmed unknown nucleic acid sequences electronically to a nucleic acid identification database having a search program, the search program producing search results based on similarity of a trimmed unknown nucleic acid sequence to a known nucleic acid sequence, and receiving the search results for each of the plurality of trimmed unknown nucleic acid sequences electronically from the nucleic acid identification database;
   e) automatically choosing selective information, including similar known nucleic acid sequences, from each search result and automatically inserting the selective information from each search result into a respective first electronic spreadsheet;
   f) selecting at least one of the search results from each of the respective first electronic spreadsheets and automatically inserting the selective information about the at least one search result into a second electronic spreadsheet.

2. The method of claim 1 wherein said nucleic acid identification database is publicly accessible via the Internet.

3. The method of claim 2 wherein said nucleic acid identification database comprises the National Center for Biotechnological Information databases.

4. The method of claim 1 wherein the plurality of unknown raw nucleic acid sequences in step b) are in electronic form.

5. The method of claim 1 wherein step a) includes creating seven main directories comprising a raw nucleic acid sequence directory for storing the plurality of unknown raw nucleic acid sequences from step b), a trimmed nucleic acid sequence directory for storing the plurality of trimmed unknown nucleic acid sequences from step c), a trimming parameters directory for storing trimming parameters used in step c), a nucleic acid identification database search results directory for storing the search results from step d), a first electronic spreadsheet directory for storing first electronic spreadsheets generated in step e), a second electronic spreadsheet directory for storing the second electronic spreadsheet generated in step f), a vector directory for storing vector definitions and a temporary file storage directory for temporarily storing files.

6. The method of claim 5 further comprising creating a DNA library subdirectory in each of the raw nucleic acid sequence directory, the trimmed nucleic acid sequence directory, the trimming parameters directory and the nucleic acid identification database search results directory.

7. The method of claim 1 wherein step d) is performed at a preset later time and then steps e) and f) are performed.

8. The method of claim 1 wherein the second electronic spreadsheet in step f) includes hyperlinks to first electronic spreadsheets in step e), the search results in step d) and the nucleic acid identification database in step d).

9. The method of claim 1 wherein the search results in step d) are received in the form of an html file.

10. The method of claim 9 wherein the selective information in step e) includes a particular database that was searched, a hyperlink to the html file, a hyperlink to the nucleic acid identification database, a score that represents the number of nucleotides matching between the trimmed unknown nucleic acid sequence and the known nucleic acid sequence stored in the nucleic acid identification database, an E value that represents the probability that a random sequence of nucleotides having a length equal to a length of the trimmed unknown nucleic acid sequence would match the known nucleic acid sequence stored in the nucleic acid identification database and a textual description of the known nucleic acid sequence stored in the nucleic acid identification database.

11. The method of claim 1 wherein the trimming locations are adjustable by a user using a Trimming Interface display.

12. The method of claim 1 wherein step d) includes submitting the plurality of trimmed unknown nucleic acid sequences and receiving the search results using a web browser program and the Internet.

13. The method of claim 11 wherein the Trimming Interface display includes scroll bars for adjusting the trimming locations.

14. The method of claim 1 wherein in step f) the computer automatically selects the at least one search result and inserts it into the second electronic spreadsheet.

15. The method of claim 1 wherein in step f) a user selects the at least one search result.

16. A computer readable medium containing a computer program for performing the method of claim 1.

* * * * *

SEQUENCE LISTING

```
<160> NUMBER OF SEQ ID NOS: 16

<210> SEQ ID NO 1
<211> LENGTH: 404
<212> TYPE: DNA
<213> ORGANISM: Unknown Organism
<220> FEATURE:
<223> OTHER INFORMATION: Description of Unknown Organism: Comparative
      DNA sequence
<220> FEATURE:
<221> NAME/KEY: modified_base
<222> LOCATION: (71)
<223> OTHER INFORMATION: a, t, c or g
<220> FEATURE:
<221> NAME/KEY: modified_base
<222> LOCATION: (142)
<223> OTHER INFORMATION: a, t, c or g
<220> FEATURE:
<221> NAME/KEY: modified_base
<222> LOCATION: (224)..(225)
<223> OTHER INFORMATION: a, t, c or g
```

```
<220> FEATURE:
<221> NAME/KEY: modified_base
<222> LOCATION: (237)
<223> OTHER INFORMATION: a, t, c or g
<220> FEATURE:
<221> NAME/KEY: modified_base
<222> LOCATION: (289)
<223> OTHER INFORMATION: a, t, c or g
<220> FEATURE:
<221> NAME/KEY: modified_base
<222> LOCATION: (297)
<223> OTHER INFORMATION: a, t, c or g
<220> FEATURE:
<221> NAME/KEY: modified_base
<222> LOCATION: (301)
<223> OTHER INFORMATION: a, t, c or g
<220> FEATURE:
<221> NAME/KEY: modified_base
<222> LOCATION: (323)
<223> OTHER INFORMATION: a, t, c or g
<220> FEATURE:
<221> NAME/KEY: modified_base
<222> LOCATION: (333)
<223> OTHER INFORMATION: a, t, c or g
<220> FEATURE:
<221> NAME/KEY: modified_base
<222> LOCATION: (350)
<223> OTHER INFORMATION: a, t, c or g
<220> FEATURE:
<221> NAME/KEY: modified_base
<222> LOCATION: (357)
<223> OTHER INFORMATION: a, t, c or g

<400> SEQUENCE: 1
gcaggttttg tgattttatt taaacataaa acatgcacac aagccatcta ctcatttcct      60
tcgctgcgta ncctggcgtt gggattggtg actctgatgg ccagctgtgc tgctctttct     120
acaatggctt ttcagttctt anaggacaca ttgtgagcaa tctcagcaca gtaagatttg     180
ttgcacatca gcagcacctc cagctccttg acattgtgga ccannaactt gcggaanccg     240
ctgggcagca tgtgcttggt tttcttgttg ctcccacaac cgaagtttng gcatcangat     300
ntggcccttg aaccttctcc ccncctgttg tcnatgcctc tgggtttccn catttcnctt     360
aatttcccat atcggtctga cttaattttc acatatcggt ctga                     404

<210> SEQ ID NO 2
<211> LENGTH: 383
<212> TYPE: DNA
<213> ORGANISM: Mus musculus

<400> SEQUENCE: 2
gcaggttttg tgattttatt taaacataaa acatgcacac aagccatcta ttcatttcct      60
tcgctgcgta gcctggcgtt gggattggtg actctgatgg ccagctgtgc tgctctttct     120
acaatggctt ttcggttctt agaggacaca ttgtgagcaa tctcagcaca gtaagatttg     180
ttgcacatca gcagcacctc cagctccttg acattgtgga ccaggaactt gcggaagccg     240
ctgggcagca tgtgcttggt tttcttgttg ctcccataac cgatgttggg catcaggatc     300
tggcccttga accttctccg caccctgttg tcaatgcctc tgggtttccg ccagtttcgc     360
ttaattttca catatcggtc tga                                             383

<210> SEQ ID NO 3
<211> LENGTH: 349
<212> TYPE: DNA
<213> ORGANISM: Unknown Organism
<220> FEATURE:
<223> OTHER INFORMATION: Description of Unknown Organism: Comparative
      DNA sequence
```

```
<220> FEATURE:
<221> NAME/KEY: modified_base
<222> LOCATION: (71)
<223> OTHER INFORMATION: a, t, c or g
<220> FEATURE:
<221> NAME/KEY: modified_base
<222> LOCATION: (142)
<223> OTHER INFORMATION: a, t, c or g
<220> FEATURE:
<221> NAME/KEY: modified_base
<222> LOCATION: (224)..(225)
<223> OTHER INFORMATION: a, t, c or g
<220> FEATURE:
<221> NAME/KEY: modified_base
<222> LOCATION: (237)
<223> OTHER INFORMATION: a, t, c or g
<220> FEATURE:
<221> NAME/KEY: modified_base
<222> LOCATION: (289)
<223> OTHER INFORMATION: a, t, c or g
<220> FEATURE:
<221> NAME/KEY: modified_base
<222> LOCATION: (297)
<223> OTHER INFORMATION: a, t, c or g
<220> FEATURE:
<221> NAME/KEY: modified_base
<222> LOCATION: (301)
<223> OTHER INFORMATION: a, t, c or g
<220> FEATURE:
<221> NAME/KEY: modified_base
<222> LOCATION: (323)
<223> OTHER INFORMATION: a, t, c or g
<220> FEATURE:
<221> NAME/KEY: modified_base
<222> LOCATION: (333)
<223> OTHER INFORMATION: a, t, c or g

<400> SEQUENCE: 3
gcaggttttg tgattttatt taaacataaa acatgcacac aagccatcta ctcattttct      60
tcgctgcgta ncctggcgtt gggattggtg actctgatgg ccagctgtgc tgctctttct     120
acaatggctt ttcagttctt anaggacaca ttgtgagcaa tctcagcaca gtaagatttg     180
ttgcacatca gcagcacctc cagctccttg acattgtgga ccannaactt gcggaanccg     240
ctgggcagca tgtgcttggt tttcttgttg ctcccacaac cgaagtttng gcatcangat     300
ntggcccttg aaccttctcc ccnnctgttg tcnatgcctc tgggtttcc                 349

<210> SEQ ID NO 4
<211> LENGTH: 349
<212> TYPE: DNA
<213> ORGANISM: Rattus sp.

<400> SEQUENCE: 4 gcagttttg tggttttatt tgaacacaaa acaggcacac aagccatcta ttcattctct       60
tcgctgcgta gcctggcgtt gggattggtg actctgatgg ccagctgtgc tgctctttct     120
acgatggctt ttcggttctt agaggacaca ttgtgagcaa tctcagcaca gtaagatttg     180
ttgcacatca gcagcacttc cagctccttg acattgtgga ccagaaactt ccggaagccg     240
ctaggcagca tgtgcttggt tttcttgtta ctcccgtaac caatgttggg catcaggatc     300
tggcccttga atcttctccg caccctgttg tcgatgcctc tgggtttcc                 349

<210> SEQ ID NO 5
<211> LENGTH: 103
<212> TYPE: DNA
<213> ORGANISM: Unknown Organism
<220> FEATURE:
<223> OTHER INFORMATION: Description of Unknown Organism: Illustrative
      DNA sequence
```

-continued

```
<400> SEQUENCE: 5
acaagctttt tttttttttt tttttttttt ttttttttgca ggttttgtga ttttatttaa      60
acataaaaca tgcacacaag ccatctactc attttcttcg ctg                        103

<210> SEQ ID NO 6
<211> LENGTH: 20
<212> TYPE: DNA
<213> ORGANISM: Unknown Organism
<220> FEATURE:
<223> OTHER INFORMATION: Description of Unknown Organism: Adapter
      sequence

<400> SEQUENCE: 6
agcggccgcc cgggcaggtc                                                   20

<210> SEQ ID NO 7
<211> LENGTH: 20
<212> TYPE: DNA
<213> ORGANISM: Unknown Organism
<220> FEATURE:
<223> OTHER INFORMATION: Description of Unknown Organism: Adapter
      sequence

<400> SEQUENCE: 7
acctcggccg cgaccacgct                                                   20

<210> SEQ ID NO 8
<211> LENGTH: 33
<212> TYPE: DNA
<213> ORGANISM: Unknown Organism
<220> FEATURE:
<223> OTHER INFORMATION: Description of Unknown Organism: Adapter
      sequence

<400> SEQUENCE: 8
ttactagtgg atccgagctc ggtaccaagc ttc                                    33

<210> SEQ ID NO 9
<211> LENGTH: 20
<212> TYPE: DNA
<213> ORGANISM: Unknown Organism
<220> FEATURE:
<223> OTHER INFORMATION: Description of Unknown Organism: Adapter
      sequence

<400> SEQUENCE: 9
agcgtggtcg cggccgaggt                                                   20

<210> SEQ ID NO 10
<211> LENGTH: 20
<212> TYPE: DNA
<213> ORGANISM: Unknown Organism
<220> FEATURE:
<223> OTHER INFORMATION: Description of Unknown Organism: Adapter
      sequence

<400> SEQUENCE: 10
acctgcccgg gcggccgctc                                                   20

<210> SEQ ID NO 11
<211> LENGTH: 33
<212> TYPE: DNA
<213> ORGANISM: Unknown Organism
<220> FEATURE:
<223> OTHER INFORMATION: Description of Unknown Organism: Adapter
```

-continued

```
                                      sequence

<400> SEQUENCE: 11
cacactggcg gccgctcgag catgcatcta gag                                      33

<210> SEQ ID NO 12
<211> LENGTH: 19
<212> TYPE: DNA
<213> ORGANISM: Unknown Organism
<220> FEATURE:
<223> OTHER INFORMATION: Description of Unknown Organism: Adapter
      sequence

<400> SEQUENCE: 12
agcggccgcc cgggcaggt                                                      19

<210> SEQ ID NO 13
<211> LENGTH: 19
<212> TYPE: DNA
<213> ORGANISM: Unknown Organism
<220> FEATURE:
<223> OTHER INFORMATION: Description of Unknown Organism: Adapter
      sequence

<400> SEQUENCE: 13
acctgcccgg gcggccgct                                                      19

<210> SEQ ID NO 14
<211> LENGTH: 624
<212> TYPE: DNA
<213> ORGANISM: Unknown Organism
<220> FEATURE:
<223> OTHER INFORMATION: Description of Unknown Organism: Illustrative
      DNA sequence
<220> FEATURE:
<221> NAME/KEY: modified_base
<222> LOCATION: (372)
<223> OTHER INFORMATION: a, t, c or g
<220> FEATURE:
<221> NAME/KEY: modified_base
<222> LOCATION: (403)
<223> OTHER INFORMATION: a, t, c or g
<220> FEATURE:
<221> NAME/KEY: modified_base
<222> LOCATION: (407)
<223> OTHER INFORMATION: a, t, c or g
<220> FEATURE:
<221> NAME/KEY: modified_base
<222> LOCATION: (434)
<223> OTHER INFORMATION: a, t, c or g
<220> FEATURE:
<221> NAME/KEY: modified_base
<222> LOCATION: (436)
<223> OTHER INFORMATION: a, t, c or g
<220> FEATURE:
<221> NAME/KEY: modified_base
<222> LOCATION: (453)
<223> OTHER INFORMATION: a, t, c or g
<220> FEATURE:
<221> NAME/KEY: modified_base
<222> LOCATION: (483)
<223> OTHER INFORMATION: a, t, c or g
<220> FEATURE:
<221> NAME/KEY: modified_base
<222> LOCATION: (492)
<223> OTHER INFORMATION: a, t, c or g
<220> FEATURE:
<221> NAME/KEY: modified_base
<222> LOCATION: (500)
<223> OTHER INFORMATION: a, t, c or g
<220> FEATURE:
<221> NAME/KEY: modified_base
<222> LOCATION: (510)
```

```
<223> OTHER INFORMATION: a, t, c or g
<220> FEATURE:
<221> NAME/KEY: modified_base
<222> LOCATION: (524)
<223> OTHER INFORMATION: a, t, c or g
<220> FEATURE:
<221> NAME/KEY: modified_base
<222> LOCATION: (537)
<223> OTHER INFORMATION: a, t, c or g
<220> FEATURE:
<221> NAME/KEY: modified_base
<222> LOCATION: (546)
<223> OTHER INFORMATION: a, t, c or g
<220> FEATURE:
<221> NAME/KEY: modified_base
<222> LOCATION: (550)
<223> OTHER INFORMATION: a, t, c or g
<220> FEATURE:
<221> NAME/KEY: modified_base
<222> LOCATION: (560)
<223> OTHER INFORMATION: a, t, c or g
<220> FEATURE:
<221> NAME/KEY: modified_base
<222> LOCATION: (570)
<223> OTHER INFORMATION: a, t, c or g
<220> FEATURE:
<221> NAME/KEY: modified_base
<222> LOCATION: (575)
<223> OTHER INFORMATION: a, t, c or g
<220> FEATURE:
<221> NAME/KEY: modified_base
<222> LOCATION: (613)
<223> OTHER INFORMATION: a, t, c or g

<400> SEQUENCE: 14
ttagcgtggt cgcggccgag gtacagaaca ctgacaaaca aggaaagcgg cagagaaaga      60
agaaagacct agaaggttgt agatgggaaa tcaggaatga tttgaactga taaagatttc     120
ggactcataa gaacacattt tataaatgtt aaacacaaaa actacatgac tgaagataga     180
agagaatgcg atggatttta ttacacatgg tggaagagag aagaggcgtg taggtttgca     240
aacaaagtta agaaatagga aactgaattt ttcattgtac agaaaatgta tctcttgggg     300
aaggcctgtg tacctgcccg ggcggccgct cgaaattcca gcacactggc ggccgttact     360
agtggatccc anctcggtac caagcttggg gttatcatgg tcntaanctg tttcctgtgt     420
gaaattgtta tccncncccc attcccccc acnttccaac ccgaaacctt aaattttaa     480 ccngggtgc cnaatgaatn acccacccn ttattgcttt gccncctgcc ccttccntcg     540
gaaccntctn cccctctttn taaaccgccn ccccnggaaa gcgtttctttt tggcccctcc     600 cctccccctc ctnatcctgc ccct                                          624

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 15
ttactagtgg atccgagctc ggtaccaagc tt                                  32

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 16
ttcgaaccat ggctcgagcc                    20